United States Patent
Desaute et al.

(10) Patent No.: US 11,864,940 B2
(45) Date of Patent: Jan. 9, 2024

(54) METHOD OF RADIOGRAPHY OF AN ORGAN OF A PATIENT

(71) Applicant: EOS IMAGING, Paris (FR)

(72) Inventors: Pascal Desaute, Paris (FR); Camille Metz, Rueil Malmaison (FR)

(73) Assignee: EOS IMAGING, Paris (FR)

( * ) Notice: Subject to any disclaimer, the term of this patent is extended or adjusted under 35 U.S.C. 154(b) by 389 days.

(21) Appl. No.: 16/628,410

(22) PCT Filed: Jul. 4, 2017

(86) PCT No.: PCT/IB2017/000986
§ 371 (c)(1),
(2) Date: Jan. 3, 2020

(87) PCT Pub. No.: WO2019/008407
PCT Pub. Date: Jan. 10, 2019

(65) Prior Publication Data
US 2020/0163643 A1    May 28, 2020

(51) Int. Cl.
*A61B 6/00*  (2006.01)
*A61B 5/055*  (2006.01)
*A61B 6/03*  (2006.01)

(52) U.S. Cl.
CPC .......... *A61B 6/5282* (2013.01); *A61B 6/4233* (2013.01); *A61B 6/466* (2013.01);
(Continued)

(58) Field of Classification Search
CPC ..... A61B 6/5282; A61B 6/4233; A61B 6/466; A61B 6/482; A61B 6/50; A61B 6/5205;
(Continued)

(56) References Cited

U.S. PATENT DOCUMENTS

2006/0008046 A1   1/2006   Ruhrnschopf
2007/0253524 A1   11/2007  Bruder et al.
(Continued)

FOREIGN PATENT DOCUMENTS

GB     2484355 A      4/2012
JP     2017074452 A   4/2017

OTHER PUBLICATIONS

Petersilka et al., Scatter correction in dual source CT, Nov. 2010, Med. Phys. vol. 37, pp. 5791-5992. (Year: 2010).*
(Continued)

*Primary Examiner* — Christine S. Kim
(74) *Attorney, Agent, or Firm* — NIXON & VANDERHYE

(57) ABSTRACT

Disclosed is a method of radiography of an organ of a patient, including: first and second vertical scanning being performed synchronously, wherein a computed correction is processed on both first and second raw images, on at least part of patient scanned height, for at least overweight or obese patients, so as to reduce, between first and second corrected images, cross-scattering existing between the first and second raw images, and wherein the computed correction processing on both the first and second raw images includes: a step of making a patient specific modeling, using as patient specific data therefore at least both first and second raw images, a step of determining a patient specific representation of radiation scattering by the patient specific modeling, a step of processing the patient specific radiation scattering representation on both the first and second raw images so as to get the first and second corrected images.

30 Claims, 19 Drawing Sheets

(52) U.S. Cl.
CPC ............... *A61B 6/482* (2013.01); *A61B 6/50* (2013.01); *A61B 6/5205* (2013.01); *A61B 6/5235* (2013.01); *A61B 6/5247* (2013.01); *A61B 6/544* (2013.01); *A61B 5/055* (2013.01); *A61B 6/032* (2013.01)

(58) Field of Classification Search
CPC ..... A61B 6/5235; A61B 6/032; A61B 6/5294; A61B 6/4014; A61B 6/022; G06T 2207/10116; G06T 2207/20128; G06T 17/00; G09B 23/28
See application file for complete search history.

(56) References Cited

U.S. PATENT DOCUMENTS

| | | | |
|---|---|---|---|
| 2008/0253515 A1 | 10/2008 | Bertram et al. | |
| 2010/0034353 A1* | 2/2010 | Kravis | G01V 5/0025 378/87 |
| 2010/0177948 A1 | 7/2010 | Le Bras | |
| 2017/0033148 A1* | 2/2017 | Liu | H01L 21/02381 |

OTHER PUBLICATIONS

Petersilka et al., Strategies for Scatter Correction in Dual Source CT, Oct. 28, 2010, Med. Phys., vol. 37, pp. 5971-5992. (Year: 2010).*
International Search Report, dated Jun. 22, 2018, from corresponding PCT application No. PCT/IB2017/000986.

* cited by examiner

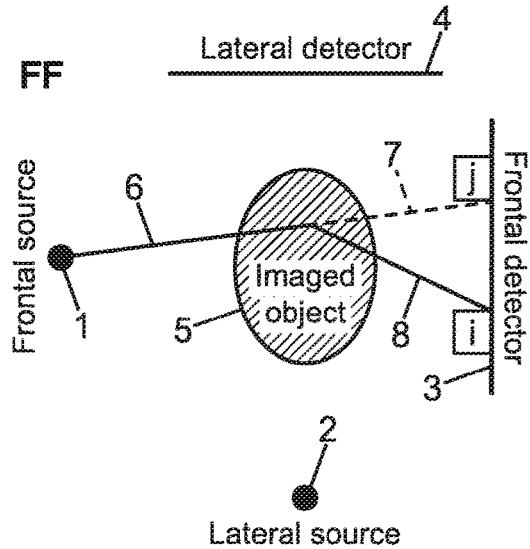
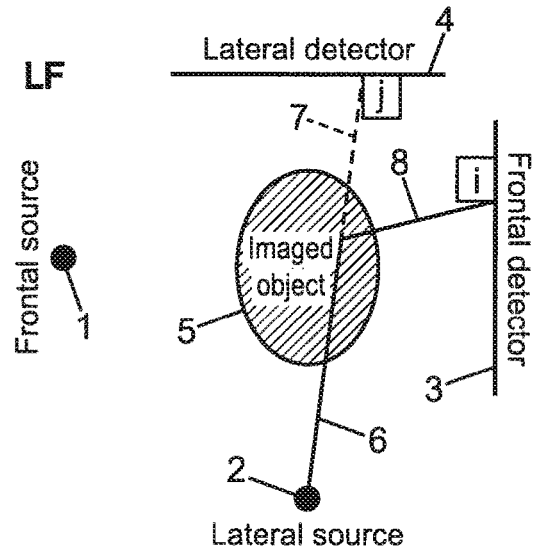
FIG. 2A  FIG. 2B
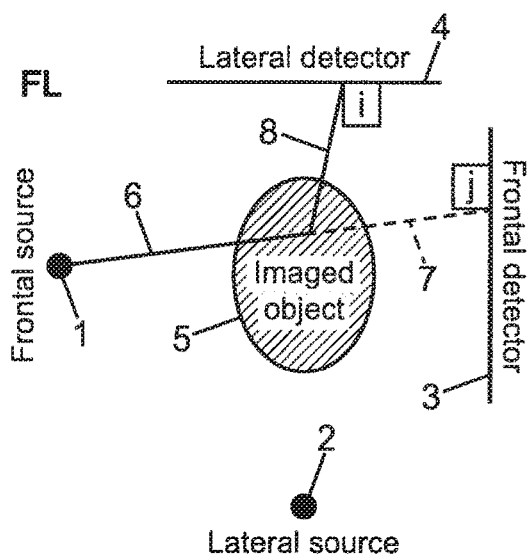
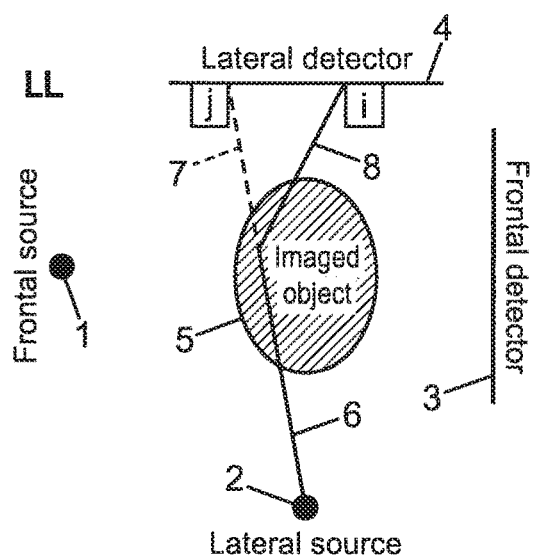
FIG. 2C  FIG. 2D $$I_0 = \begin{bmatrix} I_{0F} \\ I_{0L} \end{bmatrix} \quad I = \begin{bmatrix} I_F \\ I_L \end{bmatrix}$$

| Real spectrum\RMSE | 50keV | 60keV | 70keV | 80keV | 90keV | 100keV |
|---|---|---|---|---|---|---|
| 95kVp + Cu | 5.13% | 1.63% | 3.11% | 3.65% | 3.95% | 4.16% |
| 120kVp + Cu | 10.46% | 0.624% | 1.76% | 2.31% | 2.61% | 2.82% |
FIG. 13c
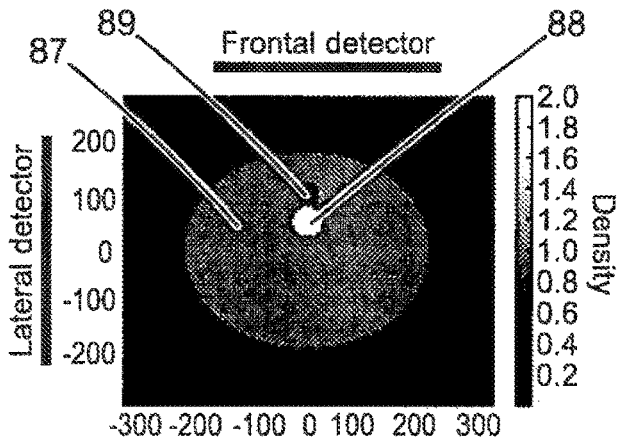
FIG. 14a
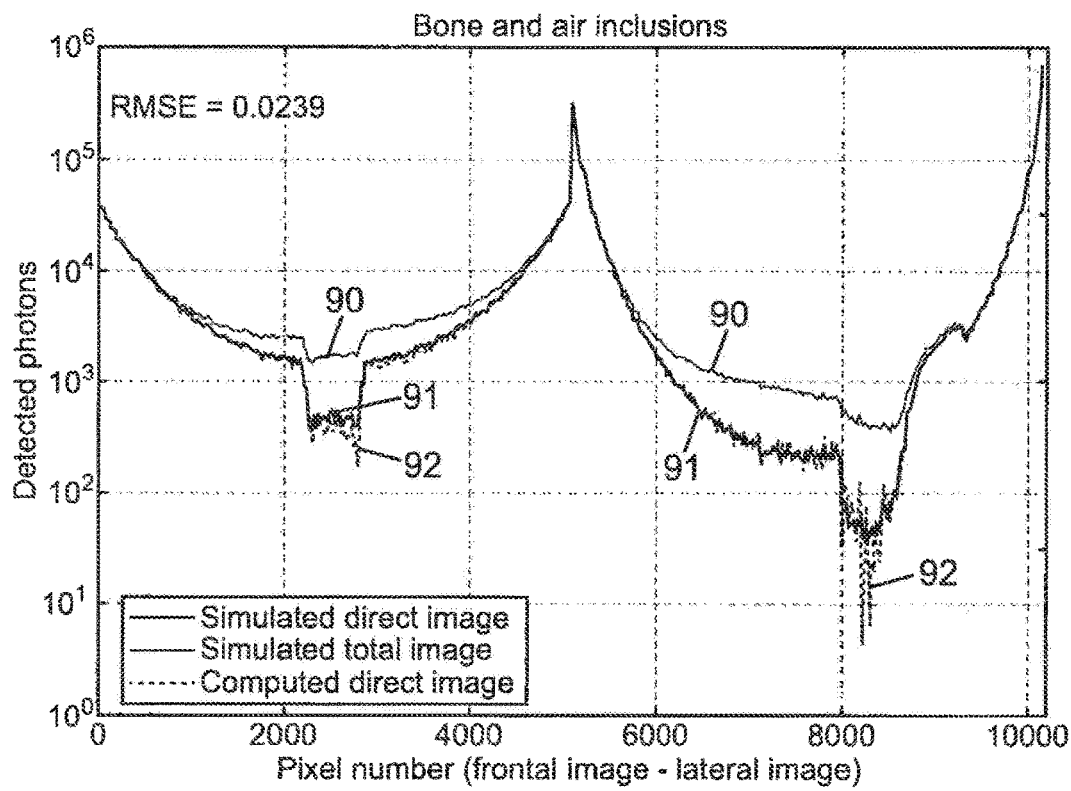
FIG. 14b

METHOD OF RADIOGRAPHY OF AN ORGAN OF A PATIENT

FIELD OF THE INVENTION

The invention relates to methods of radiography of an organ of a patient, as well as associated apparatus, in particular when the patient is an overweight or obese patient. In particular, this method of radiography is preferably a stereo-radiography method.

BACKGROUND OF THE INVENTION

The field of the invention deals with a double scanning, preferably stereo-radiographic, system and a method to optimize the radiation, preferably x-ray, scattering rejection and correction in order to acquire at least two simultaneous views, preferably frontal and lateral view images for low dose three dimensional reconstruction of an organ, preferably the skeleton, of patients for medical applications.

This system and method are dedicated to be used within medical radiology devices including at least two radiations, preferably x-ray, transmissions based imaging capabilities. These capabilities will be based on for example at least an x-ray emission source emitting x-ray spectra having a higher energy comprised between 20 keV and 200 keV. The typical imaged object is a patient in weight bearing position.

Overweight and obese patients have a larger and thicker body which will present specific challenges to methods of radiography of an organ of a patient, all the more that these overweight and obese patients are becoming more and more numerous. Indeed, according to the World Health Organization last report on obesity in 2015, worldwide obesity has more than doubled since 1980, more than 1.9 billion adults were overweight in 2014. Among these, over 600 million were obese. The World Health Organization forecasts by 2030 are very pessimistic, with a huge rise of obesity in Europe with for instance almost 74% of the population in United Kingdom would be overweight, 89% of the population of Ireland would be overweight and 50% among these would be clinically obese.

A scanning stereo-radiographic system such as the one described in EP 2309462 demonstrated good capabilities to make simultaneous frontal and lateral images for three dimensional reconstruction of skeletal anatomical parts such as the spine or pelvis with a dose reduction up to 600 compared to Computed Tomography scan, and also a dose reduction up to 10 for single view images compared to Computed Radiography or Digital Radiography systems. But the maximum available dose rate of this system has also become a growing limitation to produce enough clinical quality images of overweight and obese patients, all the more that overweight and obese patients are nowadays very common patients.

One important problem to make some good clinical quality radiology images on overweight and obese patients is the big amount of scattered x-rays created while the direct x-ray beam is much attenuated. Thus, the transmitted direct x-ray signal can become very small, typically 10-20 times lower, in comparison with the scattered x-ray signal in direct two dimensional imaging systems.

Some scattering rejection grids are commonly used to solve this problem, but taken alone, their efficiency is not good enough, and therefore the dose on overweight and obese patients can become very high in order to get clinical quality images.

A scanning stereo-radiographic system such as the one described in EP 2309462 demonstrates an efficient scattered x-ray rejection using a very thin object and detector collimations. But the useful dose rate fraction to make the image becomes too small for overweight patients. Some of the reasons are the limited output power of x-ray tubes and the very small collimation apertures.

According to such a prior art, for example described in EP 2309462, there is described a radiology method performing vertical scanning. This radiology method used collimators located upstream detectors, thereby improving cross-scattering and self-scattering rejection. However, high rejection rate was achieved thanks to narrow collimation thereby at the expense of lowering much the level of received radiation signal on the sensitive surfaces of the detectors. Therefore, at least for some patient organs, when used with reasonably overweight patients, it was difficult, and when used with really overweight or even obese patients, it was not possible, to find a good compromise between a high rate of scattering rejection and simultaneously a sufficient level of received radiation signal on the sensitive surfaces of the detectors.

A system to tune the aperture of the collimation according to the patient morphology such as the one described in another prior art, for example described in WO 2011/138632, could be used to enhance the ability to make clinical quality images on overweight patients of the scanning stereo-radiographic system described in EP 2309462.

But, in this case, the output power of the x-ray tube and available collimation aperture of the detector would not be enough to cover the whole growing population of the varied morphologies among overweight and obese patients. The aperture limitation will be directly linked with the loss of spatial resolution of the detector and the amount of scattered x-ray coming from both x-ray imaging frontal and lateral views. The use of coplanar simultaneous frontal and lateral x-ray views will create a specific problem of cross-scattering in addition to the self-scattering pollution of each view.

SUMMARY OF THE INVENTION

The object of the present invention is to alleviate at least partly the above mentioned drawbacks.

More particularly, the invention aims at providing for a radiology method which allows, for all or most of types of patient organ, for all or most types of patient morphology, including overweight and preferably obese patients, for simultaneously achieving both a received signal level on sensitive surfaces of detectors sufficiently high and a cross-scattering rejection rate sufficiently high, so as to get a good signal to noise ratio and a good image quality.

According to another prior art, described in application PCT/FR2016/050296, incorporated by reference and owned by same applicant EOS-Imaging, not yet published at time of present filing, it is known to use a vertical gap between frontal and lateral views in order to reduce cross-scattering existing between frontal and lateral raw images.

Therefore, the invention provides for processing a computed correction between first and second vertical scanning reducing, preferably drastically reducing, either with or without the help of collimation tunnels located upstream detectors, at least the cross-scattering between first and second images.

This computed correction may be used instead of the vertical gap, and thereby may provide for similar good results, with respect to reduction of cross-scattering existing between first and second raw images, with a structurally simpler apparatus, as well as with cancellation of risk of getting a slightly blurred image in case of patient moving notably during the small time shift associated to vertical gap between first vertical scanning and second vertical scanning.

This computed correction may be used in combination of the vertical gap, and thereby provide for even better results than with either the vertical gap alone or the computed correction alone, with respect to reduction of cross-scattering existing between first and second raw images.

Embodiments of the invention are dedicated to enhance greatly the capability to make improved and good clinical quality images of simultaneous frontal and lateral views on standard patients and on overweight and obese patients, improving both spatial resolution, Signal to Noise Ratio and contrast of images while simultaneously reducing the image quality loss due to cross-scattered and self-scattered radiation, preferably x-ray radiation.

This object is achieved with a method of radiography of an organ of a patient, comprising: a first vertical scanning of said organ by a first radiation source and a first detector cooperating to make a first two dimensional raw image of said organ, a second vertical scanning of said organ by a second radiation source and a second detector cooperating to make a second two dimensional raw image of said organ, said first vertical scanning and said second vertical scanning being performed synchronously, said first and second raw images viewing said organ of said patient according to different angles of incidence, wherein a computed correction is processed on both said first and second raw images, on at least part of patient scanned height, for at least overweight or obese patients, so as to reduce, between first and second corrected images, cross-scattering existing between said first and second raw images, and wherein said computed correction processing on both said first and second raw images comprises: a step of making a patient specific modeling, using as patient specific data therefore at least both first and second raw images, preferably mainly both first and second raw images, more preferably only both first and second raw images, a step of determining a patient specific representation of radiation scattering by said patient specific modeling, a step of processing said patient specific radiation scattering representation on both said first and second raw images so as to get said first and second corrected images.

This object is also achieved with a method of radiography of an organ of a patient, comprising: a first vertical scanning of said organ by a first radiation source and a first detector cooperating to make a first two dimensional raw image of said organ, a second vertical scanning of said organ by a second radiation source and a second detector cooperating to make a second two dimensional raw image of said organ, said first vertical scanning and said second vertical scanning being performed synchronously, said first and second raw images viewing said organ of said patient according to different angles of incidence, wherein a computed correction is processed on both said first and second raw images, on at least part of patient scanned height, for at least overweight or obese patients, so as to reduce, between first and second corrected images, cross-scattering existing between said first and second raw images, and wherein said computed correction processing on both said first and second raw images comprises: a step of computing only an under-sampled patient specific representation of radiation scattering, as compared to sample rate(s) of said first and second raw images, a step of over sampling said computed under-sampled patient specific radiation scattering representation so as to get same sample rate(s) as said first and second raw images, a step of processing said over sampled patient specific radiation scattering representation on both said first and second raw images so as to get said first and second corrected images. Indeed, the under-sampling of the radiation scattering representation, as compared to the raw images, allows for an important gain of computing time, at the cost of little imaging quality loss, because the spatial variation of radiation scattering is low. Preferably, said computed correction is processed on both said first and second raw images, on at least part of patient scanned height, for at least overweight or obese patients, so as to also reduce, both in said first and second corrected images, respectively self-scattering existing in both said first and second raw images.

This object is also achieved with a radiography apparatus adapted to implement a method of radiography of an organ of a patient according to the invention.

This object is also achieved with a radiography apparatus implementing a method of radiography of an organ of a patient according to the invention.

Another object of the invention is the gain in computing time and in memory size, got from the under-sampling. Therefore, this other object of the invention is achieved with a method of radiography of an organ of a patient, comprising: making a first two dimensional raw image of said organ by cooperation of a first radiation source and a first detector, making a second two dimensional raw image of said organ by cooperation of a second radiation source and a second detector, said first and second raw images viewing said organ of said patient according to different angles of incidence, wherein a computed correction is processed on both said first and second raw images, on at least part of patient scanned height, for at least overweight or obese patients, so as to reduce, between first and second corrected images, cross-scattering existing between said first and second raw images, and wherein said computed correction processing on both said first and second raw images comprises: a step of making as patient specific modeling, a 3D avatar, using both: as patient specific data therefore, at least both first and second raw images, preferably mainly both first and second raw images, more preferably only both first and second raw images, and as generic data therefore, a 3D generic model, a step of determining a patient specific representation of radiation scattering by simulating cross-scattering on said 3D avatar, a step of processing said patient specific radiation scattering representation on both said first and second raw images so as to get said first and second corrected images.

Still another object of the invention is the use of a unique and predetermined 3D avatar which will be notably richer but at the cost of a limited added complexity, because it will be unique meaning less calculation and predetermined meaning less real time calculation. Therefore, this still other object of the invention is achieved with a method of radiography of an organ of a patient, comprising: making a first two dimensional raw image of said organ by cooperation of a first radiation source and a first detector, making a second two dimensional raw image of said organ by cooperation of a second radiation source and a second detector, said first and second raw images viewing said organ of said patient according to different angles of incidence, wherein a computed correction is processed on both said first and second raw images, on at least part of patient scanned height, for at least overweight or obese patients, so as to reduce, between first and second corrected images, cross-scattering existing between said first and second raw images, and wherein said computed correction processing on both said first and second raw images comprises: a step of computing only an under-sampled patient specific representation of radiation scattering, as compared to sample rate(s) of said first and second raw images, a step of over sampling said computed under-sampled patient specific radiation scattering representation so as to get same sample rate(s) as said first and second raw images, a step of processing said over sampled patient specific radiation scattering representation on both said first and second raw images so as to get said first and second corrected images.

Preferred embodiments comprise one or more of the following features, which can be taken separately or together, either in partial combination or in full combination, with any of preceding objects of the invention.

Preferably, said computed correction is processed on both said first and second raw images, on at least part of patient scanned height, for at least overweight or obese patients, so as to also reduce, both in said first and second corrected images, respectively self-scattering existing in both said first and second raw images. This way, the computed correction not only reduces or cancels cross-scattering existing between said first and second raw images, but also reduces or cancels self-scattering existing in both said first and second raw images. The same type of computed correction is used to reduce or cancel both types of radiation scattering, cross-scattering and self-scattering.

Preferably, it comprises, before said computed correction processing, a screening including: a first step of screening, based on at least a first patient parameter representative of global patient corpulence, by: either electing said patient if said patient corresponds to an overweight or obese patient, or discarding said patient if said patient corresponds to a standard or underweight patient, a second step of screening: for said elected patient, for each of first and second raw images, by determining the location and the extent of scanned patient height to which said computed correction processing should be applied because ratio of cross-scattered and detected radiation over total detected radiation should exceed a predetermined threshold, based on at least a second patient parameter representative of patient corpulence as a function of scanned patient height, for said discarded patient, keeping unchanged said first and second raw images without applying said computed correction processing on them, it then applies, for said elected patient only, but not for said discarded patient, for each of first and second raw images, only on said determined scanned patient height, said computed correction processing on each of first and second raw images so as to get a first portion of said first and second corrected images, while keeping unchanged said first and second raw images elsewhere on scanned patient height so as to get a second portion of said first and second corrected images equal to corresponding part of said first and second raw images, and it combines, for said elected patient only, but not for said discarded patient, said first and second portions so as to get complete said first and second corrected images. Indeed, these screening steps not only discard thin patients for whom the computing correction of radiation scattering would be more or less superfluous, but also strictly limit the computing correction of radiation scattering to the portion of the patient height where it is really needed and useful.

Preferably, said first patient parameter is a patient base masse index. Indeed, this first patient parameter is well representative of the patient corpulence.

Preferably, said second patient parameter is the patient thickness, either along first direction going from center of said first radiation source to center of said first detector for first raw image or along second direction going from center of said second radiation source to center of said second detector for second raw image, as a function of scanned patient height. Indeed, this second patient parameter is well representative of the level of radiation scattering at each level of patient height.

Preferably, it comprises, before said computed correction processing, dividing each of first and second raw images into a set of raw sub-images along scanned patient height to be corrected, it comprises, for each raw sub-image of said raw image, processing said computed correction on said raw sub-image including: a step of making an under-sampled patient specific modeling, as compared to sample rate of said raw sub-image, a step of determining an under-sampled patient specific representation of radiation scattering by said under-sampled patient specific modeling, a supplementary step of over sampling said determined under-sampled patient specific radiation scattering representation so as to get same sample rate as raw image, a step of processing said over sampled patient specific radiation scattering representation on said raw sub-image so as to get a corrected sub-image, and it comprises, after processing said computed correction on all raw sub-images of said raw image, recombining said all corrected sub-images so as to get corrected image. Indeed, the under-sampling of the radiation scattering representation, as compared to the raw images, allows for an important gain of computing time, at the cost of little imaging quality loss, because of the the spatial variation of radiation scattering is slow implyinig both slow variation of radiation scattering along patient height along the slices and slow variation of radiation scattering within the plan of each slice. Dividing a raw image into a set of raw sub-images allows for simpler and more homogeneous computing in each specific raw sub-image, because the radiation scattering remains quite homogeneous over the whole extent of this specific raw sub-image. A single matrix product may be used to correct all columns of a sub-image, whether under-sampling is used or not.

Preferably, said determining step includes computing an under-sampled scattered sub-image corresponding to scattered only radiation by using a patient specific scatter matrix representing radiation scattering by said under-sampled patient specific modeling, and said processing step includes subtracting over-sampled scattered sub-image from said raw sub-image so as to get said corrected sub-image. Patient specific scatter matrix representing radiation scattering by said under-sampled patient specific modeling is under-sampled too. This is a simple way to both compute under-sampled radiation scattering while then use radiation scattering with same sample rate as raw sub-image to finally compute corrected sub-image. Indeed, this is also an interesting way to implement the radiography method of the invention with a reasonable computing time providing the definition of a matrix basis which is pre-computed with Monte Carlo simulations and which then can be used for fast computation of a solution which will be patient specific.

Preferably, under-sampling is performed with an under-sampling factor of at least 10, preferably of at least 20. This allows for an important gain of computing time as well as memory saving, when computing the radiation scattering part.

Preferably, resulting under-sampled image pixel size is at least 1 mm, preferably at least 2 mm. This allows for an important gain of computing time when computing the radiation scattering part. This also allows for putting the whole basis in memory when computing, what drastically reduces computing time.

Preferably, it comprises, before said computed correction processing, dividing each of first and second raw images into a set of raw sub-images along scanned patient height to be corrected, it comprises, for each raw sub-image of said raw image, processing said computed correction on said raw sub-image: a step of making a patient specific modeling, with same sample rate as sample rate of said raw sub-image, a step of determining a patient specific representation of radiation scattering by said patient specific modeling, with same sample rate as sample rate of said raw sub-image, a step of processing said patient specific radiation scattering representation on said raw sub-image so as to get a corrected sub-image, and it comprises, after processing said computed correction on all raw sub-images of said raw image, recombining said all corrected sub-images so as to get corrected image. Indeed, dividing a raw image into a set of raw sub-images allows for simpler and more homogeneous computing in each specific raw sub-image, because the radiation scattering remains quite homogeneous over the whole extent of this specific raw sub-image.

Preferably, said determining step includes selecting or computing a patient specific inverse matrix representing cancellation of radiation scattering by said patient specific modeling, and said processing step includes multiplying said raw sub-image by said patient specific inverse matrix so as to get said corrected sub-image. This way, fewer operations are needed to reduce or to cancel radiation scattering effect on raw images.

Preferably, said patient specific modeling for each sub-image corresponds to a nearest ellipse or to a linear combination of nearest ellipses among a predetermined family of ellipses, and said determining step includes: either selecting, in a predetermined database of matrices respectively representing radiation scattering by the ellipses of said predetermined family, one matrix and inverting it so that said inverse matrix represents cancellation of radiation scattering by said nearest ellipse, this inverse matrix thereby becoming a patient specific inverse matrix, or computing, in a predetermined database of matrices respectively representing radiation scattering by the ellipses of said predetermined family, the inverse of a linear combination of matrices respectively representing radiation scattering by said nearest ellipses of said linear combination of nearest ellipses, this inverse of linear combination of matrices thereby representing cancellation of radiation scattering by said nearest ellipses of said linear combination of nearest ellipses and becoming a patient specific inverse matrix. These ellipses offer a very good compromise between the simplicity of the performed modelling and the relevancy of this performed modelling. Besides, the use of inverse matrix allows for computing simplification. Moreover, the use of the inverse of a linear combination of matrices allows for much more precision than the use of a linear combination of inverse matrices.

Preferably, said predetermined family comprises ellipses of different sizes, of different positions within a radiography apparatus where the radiography method is performed, and of different orientations with respect to said radiography apparatus. Indeed, when only varying these three parameters for the ellipses, i.e. size, position and orientation, the used set of ellipses remains very relevant while not becoming too complex.

Preferably, density of said ellipses is sensibly equal to density of water at a pressure of 1 bar and at a temperature of 20° C. This is simple and still quite representative of a patient who is a human being.

Preferably, number of sizes is comprised between 30 and 60, the greatest ellipse axis being advantageously above 30 cm, the smallest ellipse axis being advantageously above 15 cm, and/or number of orientations is comprised between 3 and 5, and/or number of positions is comprised between 5 and 200. The set of ellipses remains of reasonable size while covering precisely most of possible patient corpulence and anatomy.

Preferably, it comprises: a step of making an under-sampled patient specific modeling, as compared to sample rate of said raw image, a step of determining an under-sampled patient specific representation of radiation scattering by said under-sampled patient specific modeling, a supplementary step of over sampling said determined under-sampled patient specific radiation scattering representation so as to get same sample rate as said raw image, a step of processing said over sampled patient specific radiation scattering representation on said raw image so as to get a corrected image. Indeed, the under-sampling of the radiation scattering representation, as compared to the raw images, allows for an important gain of computing time, at the cost of little imaging quality loss, because the spatial variation of radiation scattering is low. Richer but more complex models can be used than a specific matrix per sub-image, in order to perform patient specific modeling.

Preferably, said determining step includes first making patient specific a unique and predetermined 3D avatar at least from both first and second raw images, and then vertically scanning this patient specific 3D avatar in the same conditions as the patient but for a lower resolution allowing for under-sampling, thereby computing an under-sampled scattered image corresponding to scattered only radiation by this patient specific 3D avatar, and said processing step includes subtracting over-sampled scattered image from said raw image so as to get said corrected image. This unique and predetermined 3D avatar will be notably richer but at the cost of a limited added complexity, because it will be unique meaning less calculation and predetermined meaning less real time calculation.

In a preferred embodiment, said determining step includes first making patient specific a unique and predetermined 3D avatar using as patient specific data therefor only both first and second raw images. This will make simpler the personalization of this unique and predetermined 3D avatar to each specific patient.

In another embodiment, said determining step includes first making patient specific a unique and predetermined 3D avatar using as patient specific data, apart from both first and second raw images, also additional patient specific data coming from magnetic resonance imaging and/or from computerized tomography scan. This will make more complex but richer the personalization of this unique and predetermined 3D avatar to each specific patient.

Preferably, under-sampling is performed with an under-sampling factor of at least 10, preferably comprised between 10 and 60. This allows for an important gain of computing time when computing the radiation scattering part.

Preferably, resulting under-sampled image pixel size is at least 1 mm, preferably between 1 mm and 10 mm, more preferably between 1 mm and 6 mm. This allows for an important gain of computing time when computing the radiation scattering part.

In a first option, X-ray spectrum of first and second radiation sources, used for determining said patient specific representation of radiation scattering, has an energy comprised between 50 keV and 70 keV, preferably comprised between 55 keV and 65 keV, more preferably about 60 keV, and advantageously first and second radiation sources are monochromatic sources.

In a second option, X-ray spectrum of first and second radiation sources, used for determining said patient specific representation of radiation scattering, has a tube voltage of 120 kVolt, with a spectrum comprised between 20 keV and 120 keV, and advantageously first and second radiation sources are polychromatic sources.

In a third preferred option, on the one side for small ellipses, for the smallest half of ellipses of the basis, X-ray spectrum of first and second radiation sources, used for determining said patient specific representation of radiation scattering, has an energy comprised between 50 keV and 70 keV, preferably comprised between 55 keV and 65 keV, more preferably about 60 keV, and advantageously first and second radiation sources are monochromatic sources, whereas on the other side for big ellipses, for the biggest half of ellipses of the basis, X-ray spectrum of first and second radiation sources, used for determining said patient specific representation of radiation scattering, has a tube voltage of 120 kVolt, with a spectrum comprised between 20 keV and 120 keV, and advantageously first and second radiation sources are polychromatic sources.

This energy range is optimal in order first to get a sufficient level of signal on detectors by avoiding too much radiation absorption by the patient body as well as second to get sufficient contrast on detected images by avoiding not enough radiation absorption by the patient body.

Preferably, said method of radiography is performed with an overweight patient or with an obese patient. The method of radiography according to the invention is all the more interesting with an overweight patient or with an obese patient since, with these types of patient, there is high level of cross-scattering existing between first and second raw images.

Preferably, a collimation tunnel is located upstream each detector so as to further reduce cross-scattering on said first and second corrected images. This way, the cross-scattering level is further reduced because of the effective aperture reduction of both detectors.

Preferably, it further comprises, before said step of making a patient specific modeling from both first and second raw images, a step of denoising said first and second raw images, so as to further reduce excessive noise created by cross-scattering and/or by self-scattering on said first and second corrected images. Indeed, processing the computing correction on images previously already at least partly denoised will be more efficient, since this cancelled noise in a preliminary step will not be amplified by the further processing.

Preferably, said denoising step is a bilateral filtering of said first and second raw images. This kind of filter is a preferred example of a filter performing very well.

In a preferred embodiment, said detectors are multi-energy counting detectors. This way, it will be easier to get measures out of the corrected images, like tissue thicknesses of patient body for example.

In another embodiment, said detectors are mono-energy counting detectors.

Preferably, said detectors have more than 3000, preferably more than 5000 pixels per line. Thereby, the spatial resolution is much improved.

Preferably, said detectors have between 1 and 100 lines, preferably between 10 and 60 lines. Thereby, the complexity and the cost of detectors are kept at a limited level.

Preferably, said detectors have a pixel dimension comprised between 50 µm and 200 µm. This pixel size range is a good compromise to get all required details in the first and second corrected image while keeping at a limited level detector complexity and detector cost.

Preferably, said determining step uses a predetermined database of matrices respectively representing radiation scattering by a patient generic modeling which matrices are based on Monte-Carlo simulations of X-ray scattering. This type of simulation simulates in a very relevant way the radiation scattering. Advantageously, said Monte-Carlo simulations of X-ray scattering have been performed with an X-ray spectrum of first and second radiation sources having an energy comprised between 50 keV and 70 keV, preferably comprised between 55 keV and 65 keV, more preferably about 60 keV, and advantageously first and second radiation sources are monochromatic sources.

Preferably, said first and second raw images view said organ of said patient according to two directions orthogonal to each other.

Preferably, there is also a vertical gap between on the one hand said first source and detector and on the other hand said second source and detector, such that said first vertical scanning and said second vertical scanning are performed synchronously but with a time shift in between, so as to further reduce cross-scattering between said first and second raw images. This way, frontal and lateral corrected images take benefit of a double scatter correction, a first mechanical scatter correction and a second computing scatter correction, thereby offering a very good quality image improvement, cancelling practically all cross-scattering and most of self-scattering this way, although at the cost of some added complexity.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 2A shows schematically self-scattering existing in frontal raw image.

FIG. 2B shows schematically cross-scattering existing in frontal raw image and coming from lateral vertical scanning.

FIG. 2C shows schematically cross-scattering existing in lateral raw image and coming from frontal vertical scanning.

FIG. 2D shows schematically self-scattering existing in lateral raw image.

FIGS. 13a, 13b and 13c, show, for all pixels of the image, a comparison between different X-ray spectra of radiation sources used to determine radiation scattering, in order to evaluate best range of X-ray spectrum of radiation sources to be used to determine radiation scattering.

FIGS. 14a and 14b show, for all pixels of the image, a comparison between simulated direct image and simulated total image and computed total image, with matrix representation for received signals on frontal and lateral images, with scattered signal being under-sampled as compared to direct signal, showing the effect of bone and air inclusions.

DETAILED DESCRIPTION OF THE INVENTION

Figure 1:
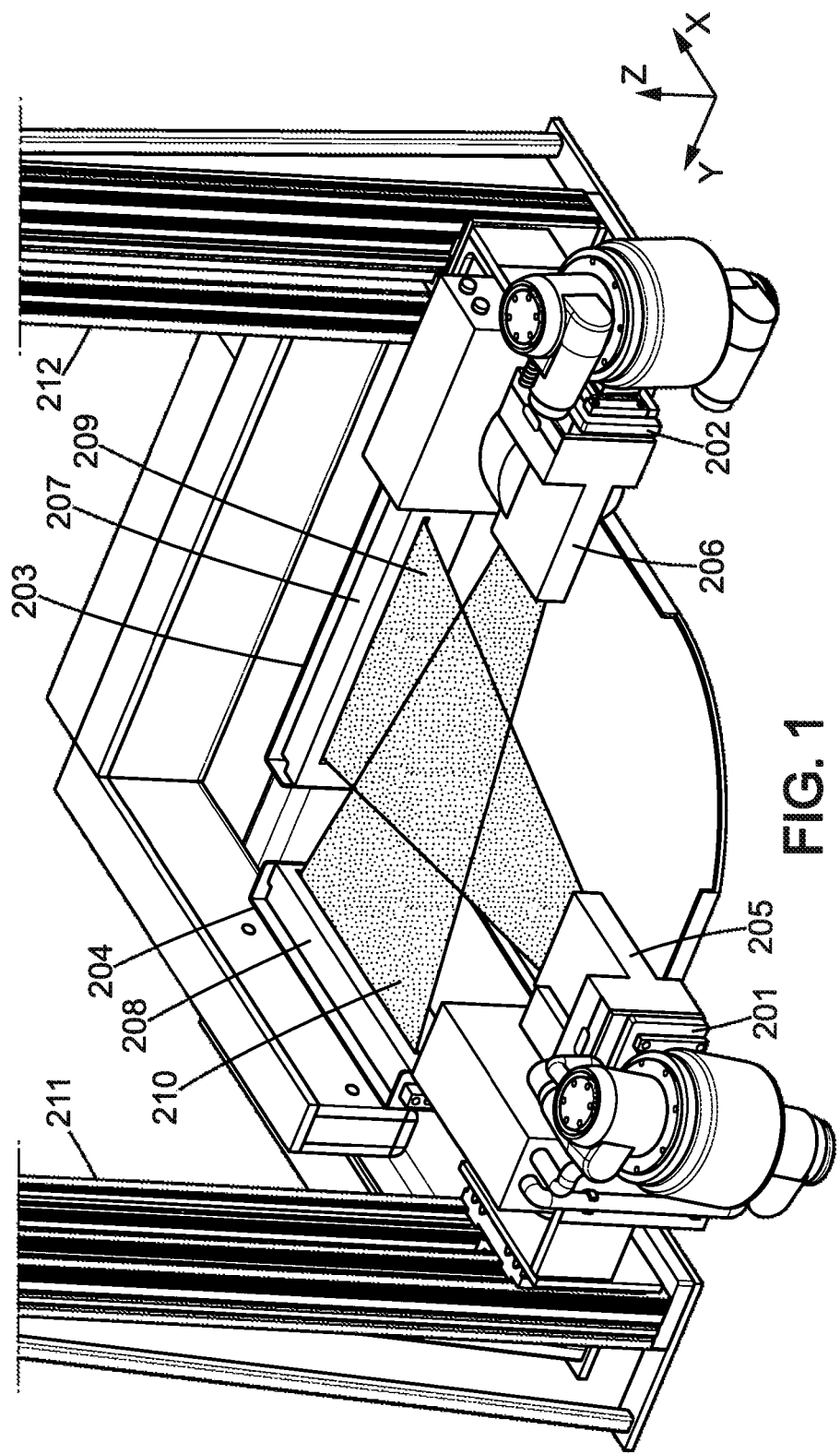
FIG. 1 shows an example of a radiology apparatus dedicated to performance of a radiology method, in which there is no vertical gap implemented between first and second vertical scanning, both first and second vertical scanning including collimation tunnels upstream the detectors, resulting in a too high cross-scattering level.

FIG. 1 shows an example of a radiology apparatus dedicated to performance of a radiology method, in which there is no vertical gap implemented between first and second vertical scanning, both first and second vertical scanning including collimation tunnels upstream the detectors, resulting in a too high cross-scattering level.

Patient will be in weight bearing position, which means patient will be standing vertically and not lying horizontally. Scanning will be performed in the vertical direction Z. Indeed, there will be both a frontal scanning giving a frontal image in the X direction and a lateral scanning giving a lateral image in the Y direction.

The radiology apparatus comprises two vertical slides 211 and 212. First vertical slide 211 is disposed for performing the frontal vertical scanning, whereas second vertical slide 212 is disposed for performing the lateral vertical scanning. Frontal vertical scanning will be performed along first vertical slide 211, whereas lateral vertical scanning will be performed along second vertical slide 212.

Along first vertical slide 211 will be translated first detection chain whereas along second vertical slide 212 will be translated second detection chain.

First detection chain comprises a first radiation source 201 associated to a first collimator 205 to narrow emitted beam 209 toward patient organ. After going through patient organ, not represented here for clarity reasons, the beam 209 enters in the first collimation tunnel 207 before reaching the sensitive surface of the first detector 203. Part of beam 209 is cross-scattered toward entering in the second collimation tunnel 208 before reaching the sensitive surface of the second detector 204. After end of first scanning, at the output of first detector 203 there is a first image, the frontal image of patient organ. The height of beam 209 considered is very small since it is the height of the beam 209 which will enter the first collimation tunnel 207 before reaching the sensitive surface of the first detector 203. Beam 209 may practically be considered as a planar beam.

Second detection chain comprises a second radiation source 202 associated to a second collimator 206 to narrow emitted beam 210 toward patient organ. After going through patient organ, not represented here for clarity reasons, the beam 210 enters in the second collimation tunnel 208 before reaching the sensitive surface of the second detector 204. Part of beam 210 is cross-scattered toward entering in the first collimation tunnel 207 before reaching the sensitive surface of the first detector 203. After end of second scanning, at the output of second detector 204 there is a second image, the lateral image of patient organ. The height of beam 210 considered is very small since it is the height of the beam 210 which will enter the second collimation tunnel 208 before reaching the sensitive surface of the second detector 204. Beam 210 may practically be considered as a planar beam.

Although a substantial part of cross-scattered signal is rejected, thanks to the presence of the collimation tunnels 207 and 208 located upstream the detectors 203 and 204, still a too important part of this cross-scattered signal is not rejected and manages to reach the sensitive surfaces of the detectors 203 and 204, thereby deteriorating the signal to noise ratio and the quality of both first frontal and second lateral images. Moreover, are also deteriorated the spatial resolution, the contrast, the detection quantum efficiency (DQE), more precisely generalized detection quantum efficiency (GDQE) or effective detection quantum efficiency (eDQE), and other parameters.

Either the tunnel collimation apertures 207 and 208 are quite wide and the level of cross-scattering is too high, at least for overweight or obese patients, at least for some organs, or the tunnel collimation apertures 207 and 208 are very narrow and the level of cross-scattering becomes acceptable, at least for overweight or obese patients, at least for some organs, but at the expense of a too low received signal on the sensitive surfaces of detectors 203 and 204.

Preferably, detectors 203 and 204 are geometrically linear detectors, and detectors 203 and 204 are preferably geometrically multi-lines linear detectors. A geometrically linear detector is a detector having a single row or several rows of aligned elementary detection units. A geometrically multi-lines linear detector is a detector having several, at least two, parallel rows of aligned elementary detection units. The multi-lines linear detector may have an output signal which is either a linear function of its input signal or a non-linear function of its input signal. That way, both the scanning image pixels dynamics and the image signal to noise ratios are improved. Yet, performing the considered vertical scanning with one line detectors, this single line being in a horizontal plan, remains possible.

The used detectors 203 and 204 present a few detection lines, typically 1 up to 100 lines, that can be used to acquire some frame images or can be summed according to a specified TDS (Time Delay Summation) or TDI (Time Delay Integration) speed in order to get a higher scanning image pixels dynamics and Signal to Noise Ratio. The effective aperture of such a detector is therefore higher than a single line detector, typically ranging from 0.1 up to 10 mm. This feature of TDS or TDI mode often provides a significant improvement in clinical quality image in comparison to detectors equipped with only one detection line for the same x-ray source output power. Other types of detectors can be used too, like for example 2D (two dimensional) detectors. The detector may be either a solid or a gaseous detector, whether 1D or 2D detector.

Preferably, collimators 205 and 206 are located downstream sources 201 and 202. That way, making the emitted radiation beams more collimated, that is more directional, the global level of scattering, either cross-scattering or self-scattering, may be further reduced.

The software correction used in the radiography method according to embodiments of the invention is based on Monte-Carlo simulations of X-ray scatter and direct signals using a modified version of MCGPU (Monte Carlo simulation of X-ray transport on a Graphics Processing Unit), a GPU-accelerated x-ray transport simulation code (implemented for Linux and CUDA) that can generate clinically-realistic radiographic projection images and computed tomography (CT) scans of the human anatomy. It simulates X-rays in a voxelized geometry and relies on PENELOPE 2006 physical models.

Radiography method according to embodiments of the invention could also be implemented using another X-ray Monte Carlo simulator such as GATE or GAMOS (based on Geant4). However, MCGPU was used rather than GATE (GPU version) with its detailed output for each simulated photon, because it reduced simulation time by a factor of about 400. That is why MCGPU has been chosen.

MCGPU open-source code is modified in order to deal with two X-ray sources placed orthogonally to simulate both the direct and self-scattered image on the one hand, and the cross-scatter on the other. The possible addition of an aperture collimation on the detector side and a physical gap between both views were implemented.

The image output was modified for a counting detector rather than an energy-integrating detector. Another output, named hereafter 'total matrix', was added: a matrix whose index (i, j) gives the number of photons detected in pixel i that were originally targeted at pixel j. With two source-detector pairs placed orthogonally on frontal and lateral views, the four matrices obtained resume to a unique one defined as follows:

$$M_{tot} = \begin{bmatrix} M_{totFF} & M_{totLF} \\ M_{totFL} & M_{totLL} \end{bmatrix},$$

obtained by Monte Carlo simulation with an uniform emission source. This matrix can be normalized in order to calculate the scatter matrix $M_{scatter}$:

$$M_{scatter} = \begin{bmatrix} M_{FF} & M_{LF} \\ M_{FL} & M_{LL} \end{bmatrix}$$

with $M_{scatter} = M_{tot} D^{-1}$, with D being the diagonal matrix of $M_{tot}$, and where $M_{FF}$ is the matrix corresponding to frontal source and detector, $M_{LF}$ to lateral source and frontal detector, $M_{FL}$ to frontal source and lateral detector and $M_{LL}$ to lateral source and detector. FIGS. 2A, 2B, 2C and 2D show graphic correspondences between on the one hand these matrices and on the other hand the different types of scattering.

FIG. 2A shows schematically self-scattering existing in frontal raw image.

There are a frontal source 1 associated to a frontal detector 3, and a lateral source 2 associated to a lateral detector 4. There is a patient body 5.

Frontal source 1 emits X-ray radiation 6, part 7 of which is directly transmitted by body 5 and arrives at pixel j on frontal detector 3, whereas part 8 of which is self-scattered by body 5 and arrives at pixel i on frontal detector 3. The radiation part 7 directly received is the useful signal, whereas the radiation part 8 which has been scattered is noise.

FIG. 2B shows schematically cross-scattering existing in frontal raw image and coming from lateral vertical scanning.

Lateral source 2 emits X-ray radiation 6, part 7 of which is directly transmitted by body 5 and arrives at pixel j on lateral detector 4, whereas part 8 of which is cross-scattered by body 5 and arrives at pixel i on frontal detector 3. The radiation part 7 directly received is the useful signal, whereas the radiation part 8 which has been scattered is noise.

FIG. 2C shows schematically cross-scattering existing in lateral raw image and coming from frontal vertical scanning.

Frontal source 1 emits X-ray radiation 6, part 7 of which is directly transmitted by body 5 and arrives at pixel j on frontal detector 3, whereas part 8 of which is cross-scattered by body 5 and arrives at pixel i on lateral detector 4. The radiation part 7 directly received is the useful signal, whereas the radiation part 8 which has been scattered is noise.

FIG. 2D shows schematically self-scattering existing in lateral raw image.

Lateral source 2 emits X-ray radiation 6, part 7 of which is directly transmitted by body 5 and arrives at pixel j on lateral detector 4, whereas part 8 of which is self-scattered by body 5 and arrives at pixel i on lateral detector 4. The radiation part 7 directly received is the useful signal, whereas the radiation part 8 which has been scattered is noise.

On FIGS. 2A to 2D, the X-ray radiation is detected at pixel i but was initially targeted at pixel j.

Figure 3A:
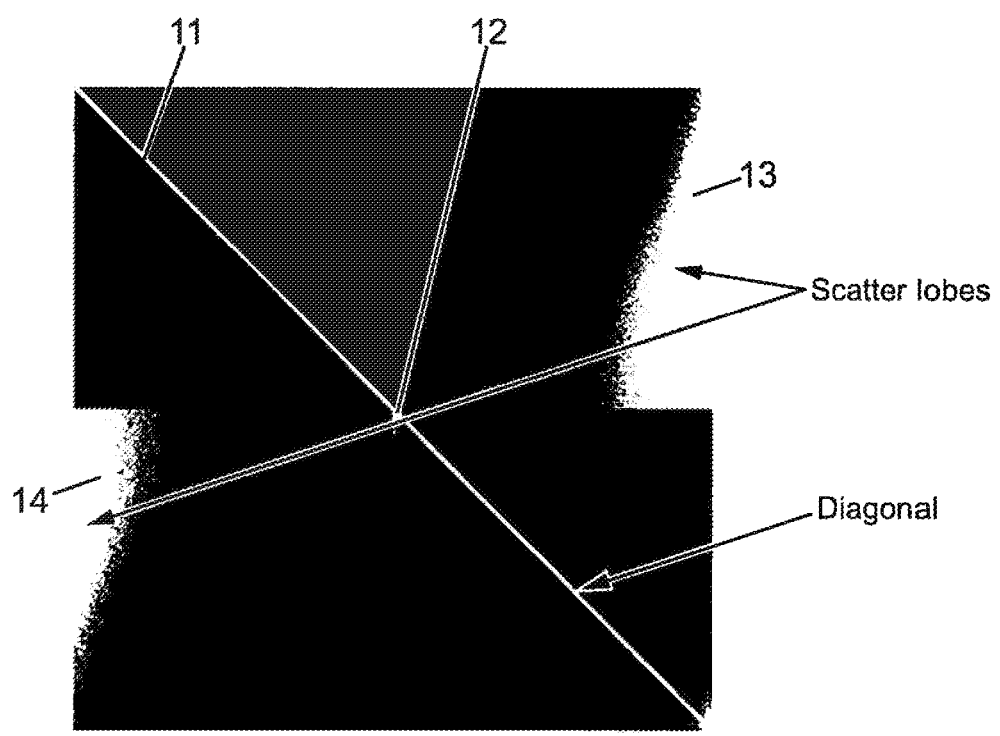
FIG. 3A shows a matrix representation of the relative importance of direct signal, self-scattering and cross-scattering.

FIG. 3A shows a matrix representation of the relative importance of direct signal, self-scattering and cross-scattering.

Patient body has been simulated by an elliptic tube presenting a cross section of 480 mm by 350 mm, the size of the detector height being 3.2 mm, the radiation sources are 60 keV monochromatic sources. There is a collimation air gap of 50 mm.

Particularly visible is the diagonal 11 that corresponds to the direct signal: all rays detected at a given pixel were originally targeted in the same direction. Every point outside the diagonal represents scatter. In particular, the two lobes 13 in the upper right and lower left 14 submatrices show the importance and the dissymmetry of cross-scatter, whereas the central larger spot 12 represents self-scatter.

A Monte Carlo simulation of an uniform source vector U where $$U = \begin{bmatrix} 1 \\ \vdots \\ 1 \end{bmatrix},$$

provides a direct signal vector $V_d$, a total signal vector $V_{tot}$, and a matrix $M_{tot}$. The repetition of simulations with movement of phantom ellipse at each step provides a scanning image.

$M_{tot}$ (i,j) is the total signal measured in pixel i created by a photon initially directed towards pixel j.

$M_{tot}$ relies U and $V_{tot}$: $V_{tot} = M_{tot} U$.

The diagonal elements vector of $M_{tot}$ is therefore the direct signal vector, which is the signal created in pixel i by a photon directed towards pixel i.

The diagonal matrix D of $M_{tot}$ relies U and $V_d$: $V_d = D U$.

The desired scatter matrix will link the direct signal to the total signal according to: $I = M_{scatter} I_0$ (first equation)

Thus the source vector U has to be removed from the equations by a normalization operation of the matrix.

This gives in a nutshell:

D(i,j)=$M_{tot}$ (i,i) if i=j or D(i,j)=0 if i is different from j $$V_d = DU \text{ and } V_{tot} = M_{tot}U \qquad \text{(second equation)}$$

what gives:

$$U = D^{-1}V_d \text{ and } V_{tot} = M_{tot}D^{-1}V_d \qquad \text{(third equation)}$$

what gives:

$$M_{scatter} = M_{tot}D^{-1} \text{ and } V_{tot} = M_{scatter}V_d$$

hence:

$$M_{scatter}(i,j) = M_{tot}(i,j)M_{tot}(j,j)$$

This last equation can be extended for an homogeneous object (for instance a vertical axis cylinder) and images by scanning, what gives:

$$V_{tot} = M_{scatter}V_d \text{ giving } I_{tot} = M_{scatter}I_d \text{ (equivalent of first equation)}$$

Figure 3B:
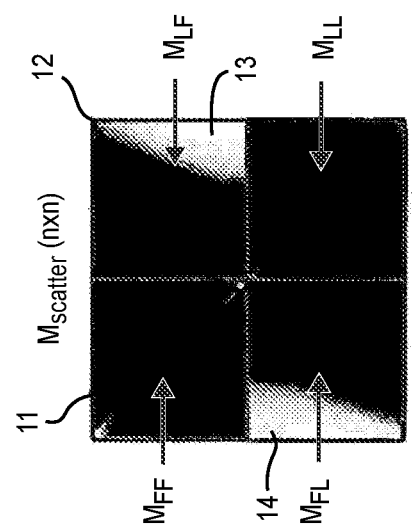
FIG. 3B shows a matrix representation of the relative importance of direct signal, self-scattering and cross-scattering, with sub-matrices representing the respective transformations undergone by the signal coming from one or the other source and detected on one or the other detector.

FIG. 3B shows a matrix representation of the relative importance of direct signal, self-scattering and cross-scattering, with sub-matrices representing the respective transformations undergone by the signal coming from one or the other source and detected on one or the other detector.

Patient body has been simulated by an elliptic tube presenting a cross section of 480 mm by 350 mm, the size of the detector height being 3.2 mm, the radiation sources are 60 keV monochromatic sources. There is a collimation air gap of 50 mm.

Particularly visible is the diagonal 11 that corresponds to the direct signal: all rays detected at a given pixel were originally targeted in the same direction. Every point outside the diagonal represents scatter. In particular, the two lobes 13 in the upper right and lower left 14 submatrices show the importance and the dissymmetry of cross-scatter, whereas the central larger spot 12 represents self-scatter.

If one considers that $I_F$ is the detected frontal image, $I_L$ is the detected lateral image, $I_{0F}$ is the direct frontal image which is the frontal image that would be detected if there were no scattering, neither cross-scattering nor self-scattering, and $I_{0L}$ is the direct lateral image which is the lateral image that would be detected if there were no scattering, neither cross-scattering nor self-scattering, then one gets the following equations:

$$I_F = M_{FF}I_{0F} + M_{LF}I_{0L}$$

$$I_L = M_{LL}I_{0L} + M_{FL}I_{0F}$$

with $M_{FF}$ the matrix representing the transformation undergone by the signal coming from frontal source and detected on frontal detector, $M_{FF}$ the matrix representing the transformation undergone by the signal coming from lateral source and detected on frontal detector, $M_{LL}$ the matrix representing the transformation undergone by the signal coming from lateral source and detected on lateral detector, $M_{FL}$ the matrix representing the transformation undergone by the signal coming from frontal source and detected on lateral detector.

Those equations lead to the equation: I=$M_{Scatter}$ I$_0$, with $$I_0 = \begin{bmatrix} I_{0F} \\ I_{0L} \end{bmatrix} \text{ and } I = \begin{bmatrix} I_F \\ I_L \end{bmatrix} \text{ and } M_{Scatter} = \begin{bmatrix} M_{FF} & M_{LF} \\ M_{FL} & M_{LL} \end{bmatrix}.$$

One preferred solution to solve this last equation is to perform direct deblurring giving the direct image by solving the equation: $\hat{I}_0 = M_{Scatter}^{-1}$ I. This solution works especially well when noise level is quite low what happens in case of using under-sampling as explained below.

Figure 3D:
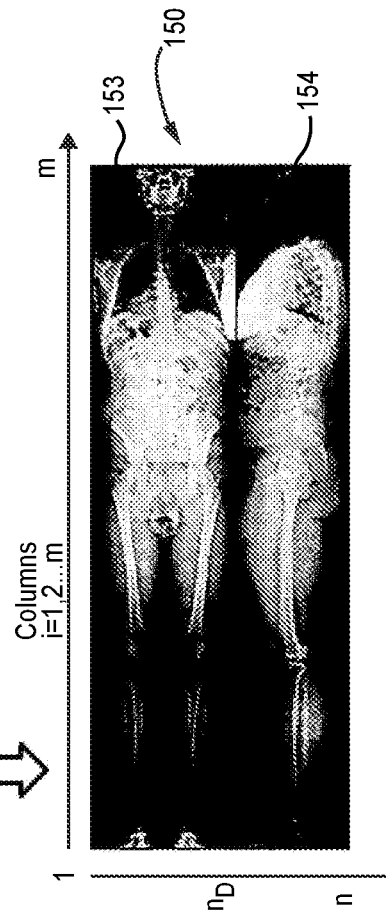
FIG. 3D shows a pair of frontal and lateral images juxtaposed together and rotated in order to get an aggregated image.
Figure 3C:
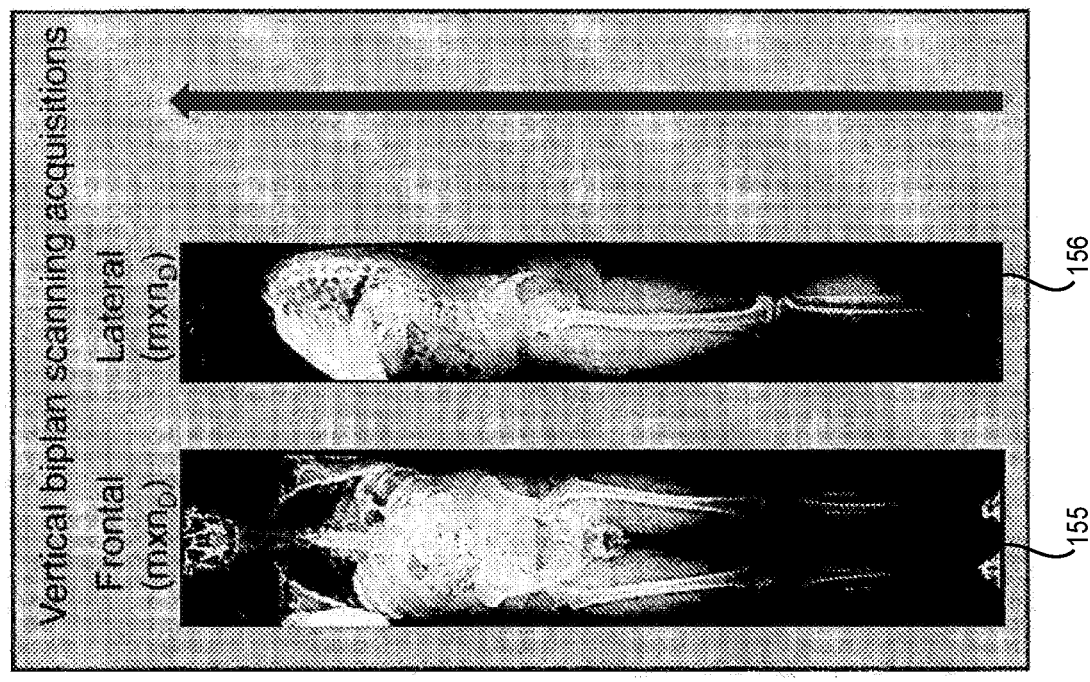
FIG. 3C shows a pair of frontal and lateral images got from a vertical scanning performed according to an embodiment of the invention.

FIG. 3C shows a pair of frontal and lateral images got from a vertical scanning performed according to an embodiment of the invention.

The frontal vertical image 155 is obtained from the frontal source and detector vertical scanning, whereas the lateral vertical image 156 is obtained from the lateral source and detector vertical scaning.

FIG. 3D shows a pair of frontal and lateral images juxtaposed together and rotated in order to get an aggregated image.

Frontal image 155 and lateral image 156 of FIG. 3C have been processed, first by being juxtaposed together and second by being rotated by a quarter of turn. The resulting image 150 is composed of the juxtaposition of two horizontal images 153 and 154 vertically juxtaposed one above the other, respectively corresponding to frontal and lateral images 155 and 156 of FIG. 3C.

Figure 3E:
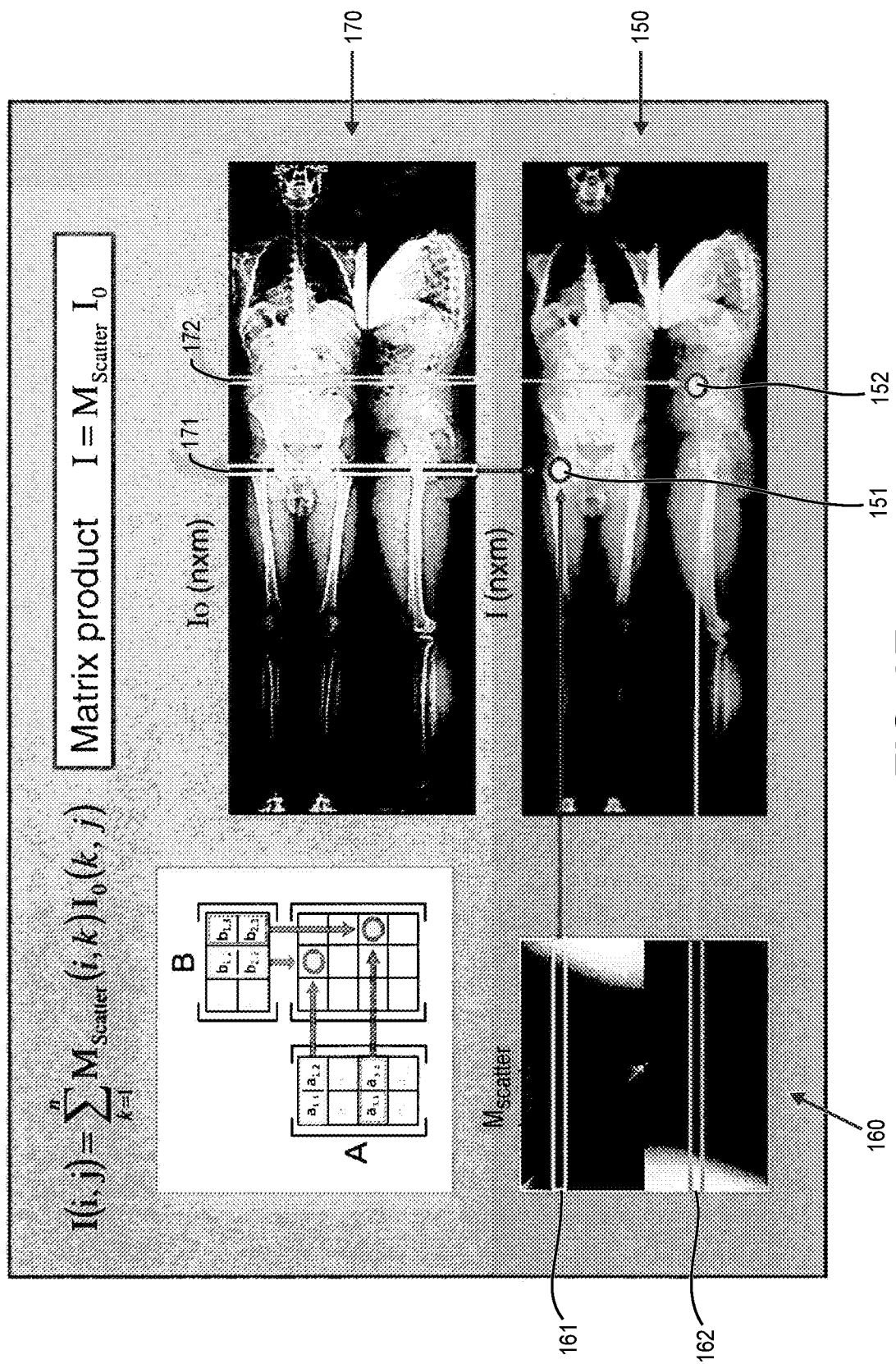
FIG. 3E shows a graphic representation of the relation existing between the direct image which would be obtained in case of absence of scattering, the blurred image obtained in presence of scattering, and the scatter matrix.

FIG. 3E shows a graphic representation of the relation existing between the direct image which would be obtained in case of absence of scattering, the blurred image obtained in presence of scattering, and the scatter matrix.

The matrix product $I_{tot} = M_{scatter} I_d$ (or I=$M_{scatter}$ I$_0$) which corresponds to $I(i,j) = \Sigma_{k=1}^{n} M_{scatter}(i,k) I_0(k,j)$, indeed:

The direct image 170 (without scattering) multiplied by the scatter matrix 160 will give the measured blurred image 150 (with scattering). Each column 171 of the direct image 170 multiplied by each line 161 of the scatter matrix 160 will give a spot 151 of the measured blurred image 150. For example, another column 172 of the direct image 170 multiplied by another line 162 of the scatter matrix 160 will give another spot 152 of the measured blurred image 150.

Figure 3F:
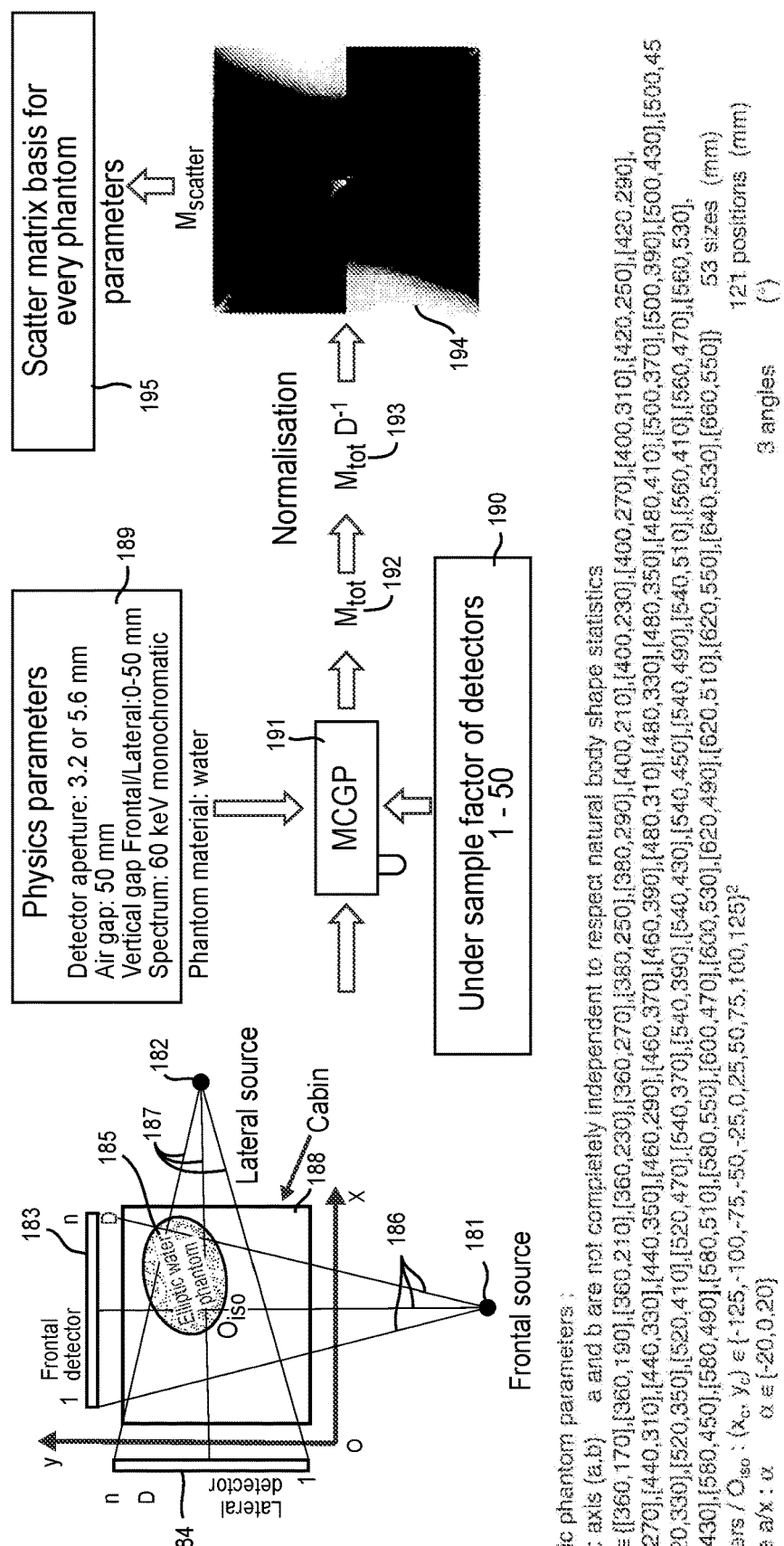
FIG. 3F shows an example of Monte Carlo simulation of X-ray transport on a Graphics Processing Unit in order to get a scatter matrix basis.

FIG. 3F shows an example of Monte Carlo simulation of X-ray transport on a Graphics Processing Unit in order to get a scatter matrix basis.

The projections of frontal 186 and lateral 187 radiation beams coming from frontal 181 and lateral 182 radiation sources on frontal 183 and lateral 184 detectors after going through an elliptic phantom material 185 located in a cabin 188 are simulated.

A Monte Carlo Graphics Processing Unit (MCGPU) 191 gets as inputs, the preceding projections, as well as an under-sampling factor 190 ranging from 1 (no under-sampling) to 50 (high under-sampling factor), and a set 189 of physics parameters including a detector aperture, for example either 3.2 mm or 5.6 mm, a detector collimation air gap, for example 50 mm, a vertical gap between frontal and lateral scannings comprised between 0 mm (preferred case) and 50 mm (as in presented prior art), a source spectrum, for example 60 keV monochromatic.

As output of this Monte Carlo Graphics Processing Unit (MCGPU) 191, there is the matrix $M_{tot}$ 192, leading by normalisation $M_{tot}$ D$^{-1}$ 193 (as seen above), to the scatter matrix $M_{scatter}$ 194, thereby allowing for construction of the scatter matrix basis 195 for each elliptic phantom contemplated.

For example, a preferred set of the elliptic phantom parameters is now given.

There are 53 sizes of elliptic phantoms, given by the couples of their big and small axes expressed in mm: (360,170), (360,190), (360,210), (360,230), (360,270), (380, 250), (380,290), (400,210), (400,230), (400,270), (400,310), (420,250), (420,290), (440,270), (440,310), (440,330), (440, 350), (460,290), (460,370), (460,390), (480,310), (480,330), (480,350), (480,410), (500, 370), (500, 390), (500, 430), (500, 450), (520, 330), (520, 350), (520, 410), (520, 470), (540, 370), (540, 390), (540, 430), (540, 450), (540, 490), (540, 510), (560, 410), (560, 470), (560, 530), (580, 430), (580, 450), (580, 490), (580, 510), (580, 550), (600, 470), (600, 530), (620, 490), (620, 510), (620, 550), (640, 530), (660, 550).

There are 11 positions with respect to the center of the cabin, for each direction x or y, what makes in combination 121 positions; those positions are for each direction x or y, expressed in mm: (−125, −100, −75, −50, −25, 0, 25, 50, 75, 100, 125).

There are 3 angles of rotation with respect to a position where the big axis of the elliptic phantom is parallel to the frontal detector and where the small axis of the elliptic phantom is parallel to the lateral detector, which are expressed in degrees with respect to preceding alignment: (−20, 0, 20).

There are all in all 16390 matrices in the matrix basis: 53 sizes multiplied by 121 positions multiplied by 3 orientations. This would need a memory size of about 6.5 To with no under-sampling (corresponding to an under-sampling factor value of 1), or of about 16 Go with an under-sampling factor of 20, or of about 4 Go with an under-sampling factor of 40, or of about 2.5 Go with an under-sampling factor of 50.

Figure 4A:
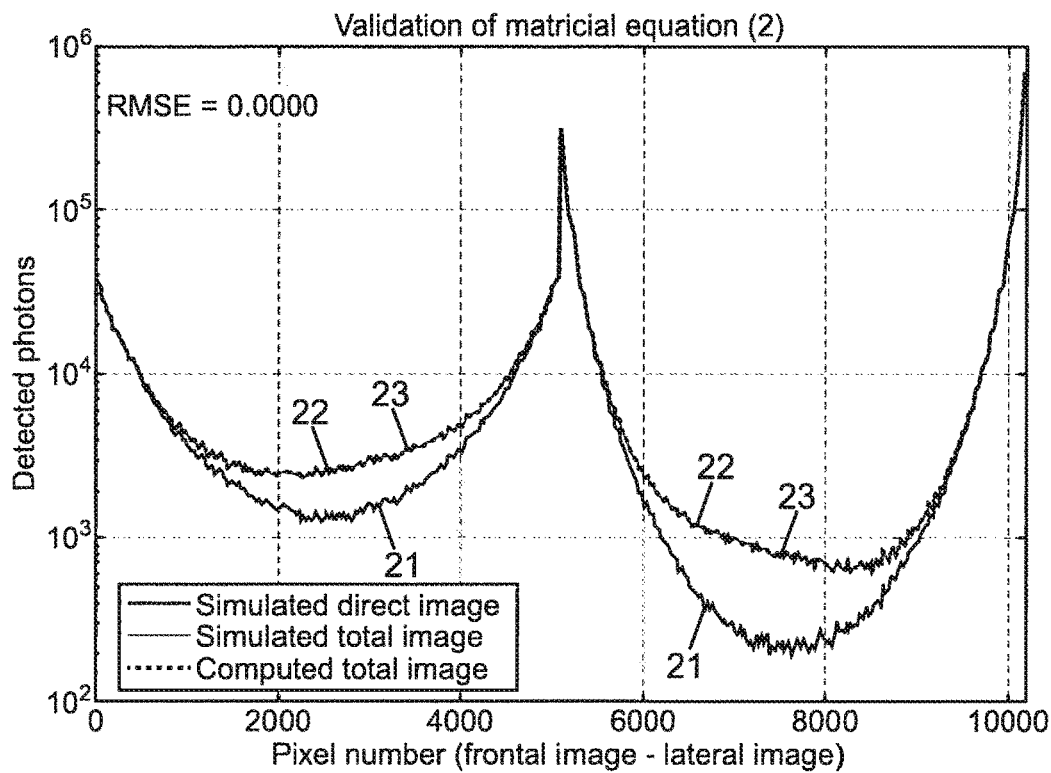
FIGS. 4a and 4b show, for all pixels of the image, a comparison between simulated direct image and simulated total image and computed total image, validating the matrix representation of the received signals on frontal and lateral images, with same sample rate between direct signal and scattered signal.
Figure 4B:
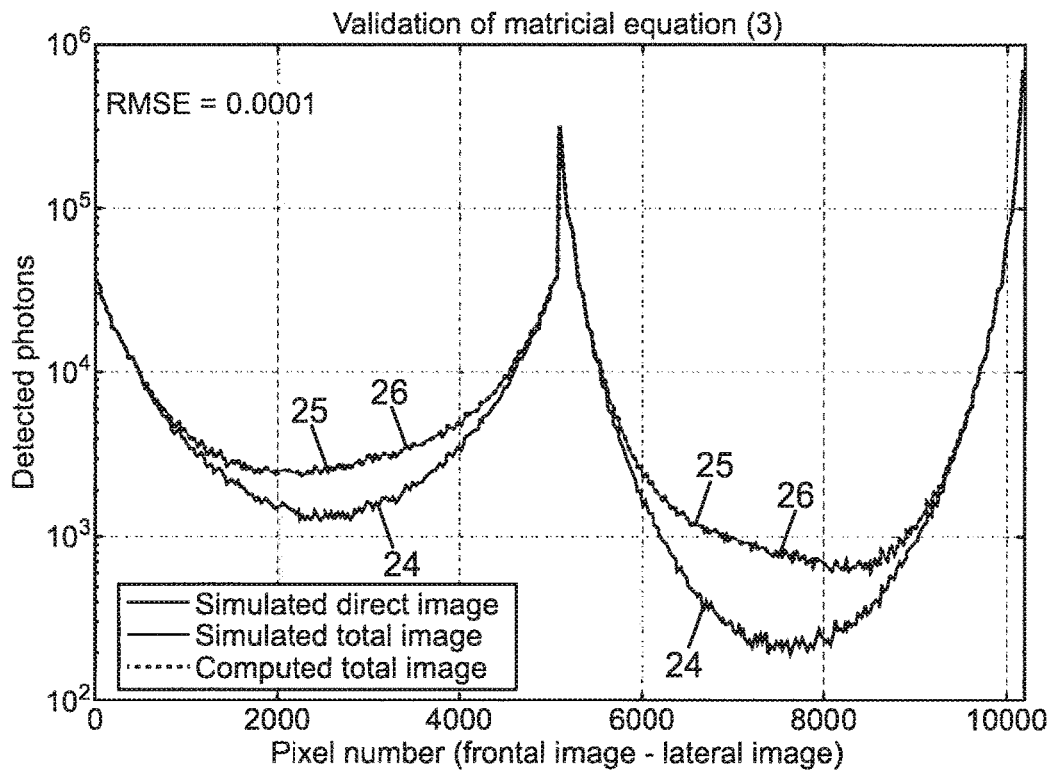

FIGS. 4a and 4b show, for all pixels of the image, a comparison between simulated direct image and simulated total image and computed total image, validating the matrix representation of the received signals on frontal and lateral images, with same sample rate between direct signal and scattered signal.

The number of detected photons is represented as a function of the position of the pixels, the pixels being numbered from 1 to a bit more than 10000, for example to about 10300, for example 10278. The simulated direct image is represented by curve 21, the simulated total image is represented by curve 22, the computed total image is represented by curve 23. Simulated image can correspond to a scanning got from repetition of the simulation, and curves are obtained either from a column vector extracted from images, or got from simulation of a single column.

FIG. 4a shows validation of second equation and FIG. 4b shows validation of third equation. Either on FIG. 4a or on FIG. 4b, the computed total signal is practically perfectly superimposed on the simulated one what is proven by the very small Root Mean Square Error (RMSE<0.01%). Indeed, on FIG. 4a, curves 22 and 23 are practically perfectly superimposed, and on FIG. 4b, curves 25 and 26 are practically perfectly superimposed too.

First equation of unknown I$_0$ is solved to get the direct image from the total one. As the scatter signal is evolving rather slowly, the solution can be computed for under-sampled images and matrices. It will be shown in next FIG. 5 that 2 mm-wide and 3.2 mm-high pixels allow for a good enough precision in the correction of images with pixels of 0.1 mm×0.1 mm.

Figure 5:
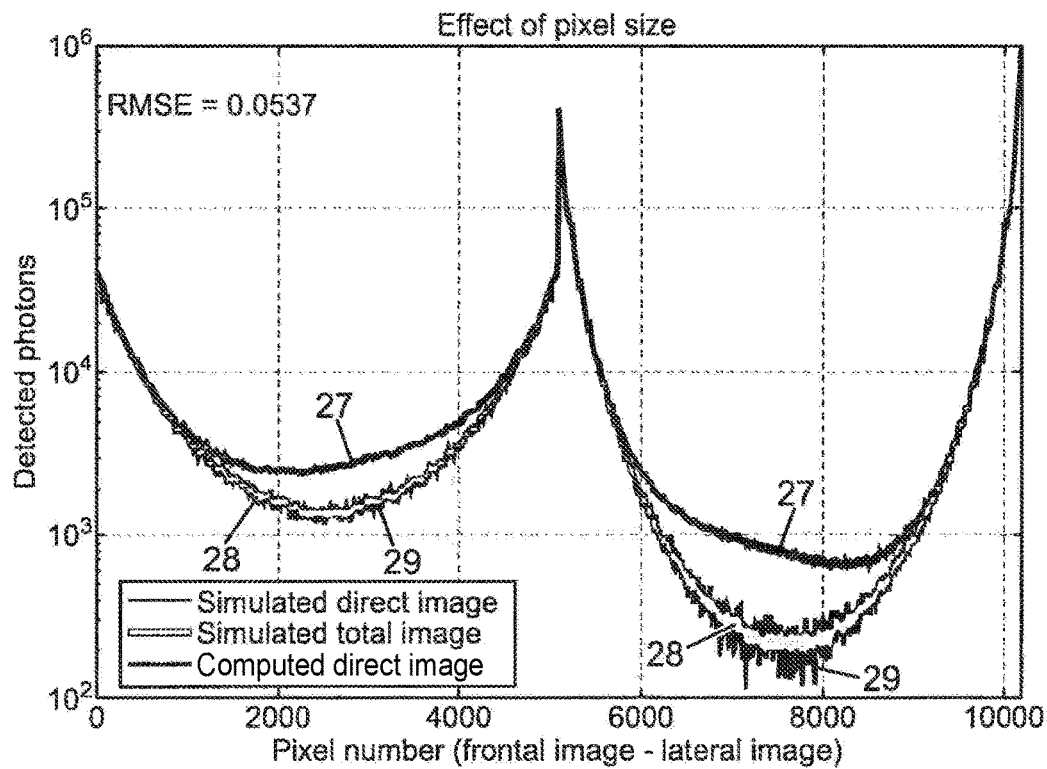
FIG. 5 shows, for all pixels of the image, a comparison between simulated direct image and simulated total image and computed direct image, with the matrix representation for received signals on frontal and lateral images, with scattered signal being under-sampled as compared to direct signal.

FIG. 5 shows, for all pixels of the image, a comparison between simulated direct image and simulated total image and computed direct image, with the matrix representation for received signals on frontal and lateral images, with scattered signal being under-sampled as compared to direct signal.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 µm pixels is corrected with a scatter matrix obtained for 2 mm large pixels, indeed with an under-sampling factor of 20.

The number of detected photons is represented as a function of the position of the pixels, the pixels being numbered from 1 to a bit more than 10000. The simulated direct image is represented by curve 28, the simulated total image is represented by curve 27, the computed direct image is represented by curve 29.

Two different methods may be used to correct a given clinical image. Either a precomputed base of matrices corresponding to simple geometries, for example ellipses filled with water, may be used to afterwards perform the matrix inversion as described below. Or a 3D (three dimensional) voxelized reconstruction, obtained from the deformation of a generic model to patient specific radiographic projections, to directly simulate the scatter signals with lower resolution and remove them from the radiological projections in order to get the direct images.

On FIG. 5, the computed direct signal is well superimposed on the simulated one what is proven by the small Root Mean Square Error (RMSE<5.4%). Indeed, on FIG. 5, curves 28 and 29 are rather well superimposed.

Figure 6:
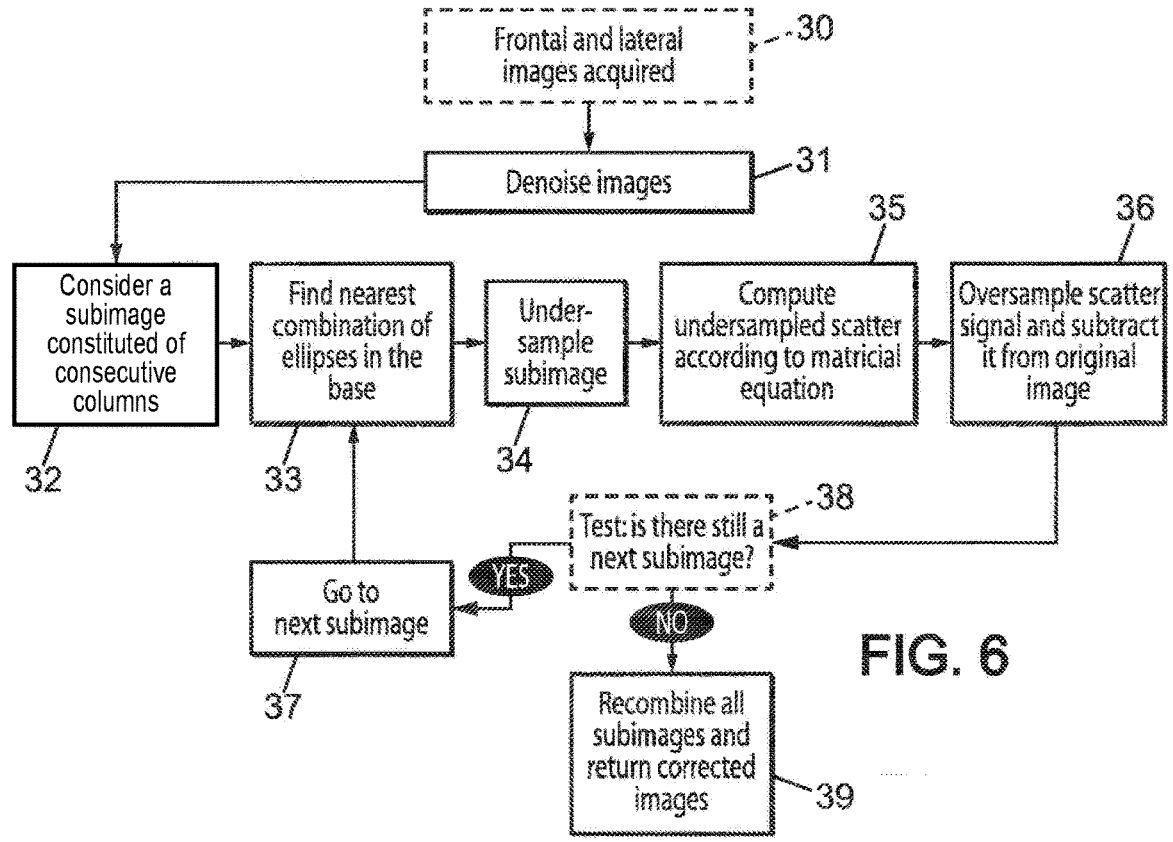
FIG. 6 shows an example of performing the steps of the method of radiography of an organ of a patient according to a first embodiment of the invention, with use of scatter matrix and with scattered signal being under-sampled as compared to direct signal.

FIG. 6 shows an example of performing the steps of the method of radiography of an organ of a patient according to a first embodiment of the invention, with use of scatter matrix and with scattered signal being under-sampled as compared to direct signal.

The different and successive steps of the scatter correction method to correct a given line of pixels on both frontal and lateral views with a preexisting matrix are hereby described.

In a step 30, frontal and lateral images are acquired.

In a step 31, those frontal and lateral images are denoised.

In a step 32, those frontal and lateral images are each divided into sub-images along vertical axis whose height is about 1 cm, representing some consecutive columns of aggregated image.

In a step 33, for each sub-image, the nearest combination of base ellipses within a predetermined family is found.

In a step 34, each sub-image is under-sampled, typically to 2 mm wide pixels.

In a step 35, either there is an under-sampling factor rather high, for instance about 10 or 20, and a direct calculation by inversion of the scatter matrix and multiplication of this inverse scatter matrix by the measured blurred image (with scattering) is the quickest way to get at the direct image (without scattering), or there is a small or no under-sampling factor, and a linear system resolution algorithm, such as preferably of the type Richardson-Lucy algorithm, more precisely the adapted Richardson-Lucy algorithm presented below, is applied to compute the under-sampled direct image given the total image and the scatter matrix. This under-sampled direct image is subtracted from the original total image to get the under-sampled scatter signal.

In this step 35, if one considers that $I_F$ is the detected frontal image, $I_L$ is the detected lateral image, $I_{0F}$ is the direct frontal image which is the frontal image that would be detected if there were no scattering, neither cross-scattering nor self-scattering, and $I_{0L}$ is the direct lateral image which is the lateral image that would be detected if there were no scattering, neither cross-scattering nor self-scattering, then one gets the following equations:

$$I_F = M_{FF} I_{0F} + M_{LF} I_{0L}$$

$$I_L = M_{LL} I_{0L} + M_{FL} I_{0F}$$

with $M_{FF}$ the matrix representing the transformation undergone by the signal coming from frontal source and detected on frontal detector, $M_{LF}$ the matrix representing the transformation undergone by the signal coming from lateral source and detected on frontal detector, $M_{LL}$ the matrix representing the transformation undergone by the signal coming from lateral source and detected on lateral detector, $M_{FL}$ the matrix representing the transformation undergone by the signal coming from frontal source and detected on lateral detector.

Those equations lead to the equation: $I = M_{Scatter} I_0$, with $$I_0 = \begin{bmatrix} I_{0F} \\ I_{0L} \end{bmatrix} \text{ and } I = \begin{bmatrix} I_F \\ I_L \end{bmatrix} \text{ and } M_{Scatter} = \begin{bmatrix} M_{FF} & M_{LF} \\ M_{FL} & M_{LL} \end{bmatrix}.$$

One solution to solve this last equation may be to perform direct deblurring giving the direct image by solving the equation: $\hat{I}_0 = M_{Scatter}^{-1} I$.

However, solving directly this last equation would give a high level of noise amplification, except in case of notable under-sampling, where this direct method is preferred. In case of absence of under-sampling, it is preferred to use an adapted Richardson Lucy algorithm to do so. The difference between a Richardson Lucy algorithm and an adapted Richardson Lucy algorithm is that a Richardson Lucy algorithm (cony being the convolution operator) is used to solve the equation: d=u cony P, by using the formula:

$$u^{t+1} = u^t [(d/[u^t \text{ conv } P]) \text{conv } ^\sim P],$$

whereas an adapted Richardson Lucy algorithm is used to solve the equation: $I = M_{Scatter} I_0$, by using the formula:

$$\hat{I}_0^{t+1} = \hat{I}_0^t [M_{Scatter}'(I/[M_{Scatter} \hat{I}_0^t])].$$

In a step 36, first this scatter signal is over-sampled by linear interpolation and the resulting signal is smoothed so as to get the oversampled scatter image, and second this oversampled scatter image is subtracted from the total image to get the oversampled direct image.

In a step 38, either there is yet a next sub-image to be processed and process goes to step 37, or there is no more sub-image to be processed and process goes to step 39.

In a step 37, the next sub-image is processed by getting back to step 33 and by applying it to this next sub-image.

In a step 39, all the sub-images are recombined together to return a corrected frontal and lateral images of the patient body.

Figure 7A:
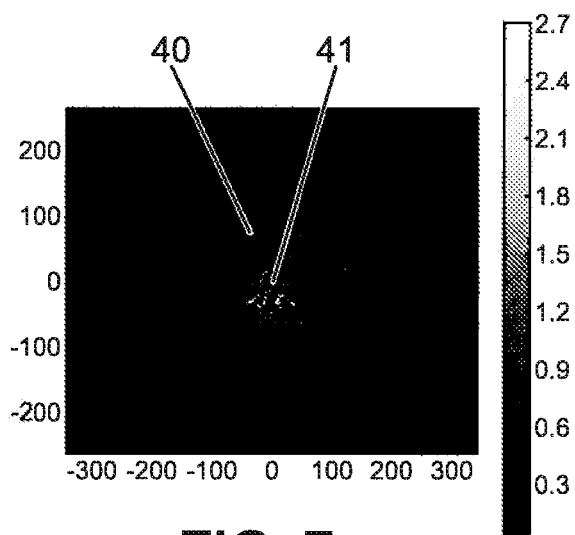
FIGS. 7a and 7b show schematically an example of a top view and of a frontal view of a sub-image when performing the steps of the method of radiography of an organ of a patient according to a first embodiment of the invention.
Figure 7B:
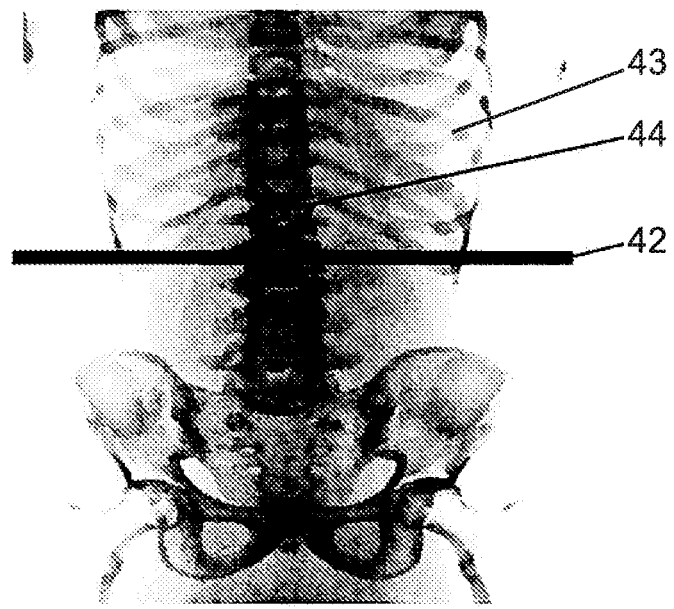

FIGS. 7a and 7b show schematically an example of a top view and of a frontal view of a sub-image when performing the steps of the method of radiography of an organ of a patient according to a first embodiment of the invention.

FIG. 7a represents a slice of a patient body, for example a slice of a patient abdomen, here showing a spine vertebra 41 among the rest of the patient body slice surface 40.

FIG. 7b represents a frontal image of this patient body, where the height of the slice 42 represented at FIG. 7a is visible. This frontal image shows, among other things, patient ribs 43 and patient spine 44.

This first embodiment method can of course be adapted to deal with full-resolution matrices. As already explained, using under-sampled matrices is more efficient because on the one hand the result remains satisfactory and on the other hand it amounts to reduce simulation times by a factor of about 20, as well as correction computations. Adaptation of the first embodiment to a second embodiment by using full resolution matrices instead of under-sampled matrices is shown in relation to FIGS. 8 and 9.

Figure 8:
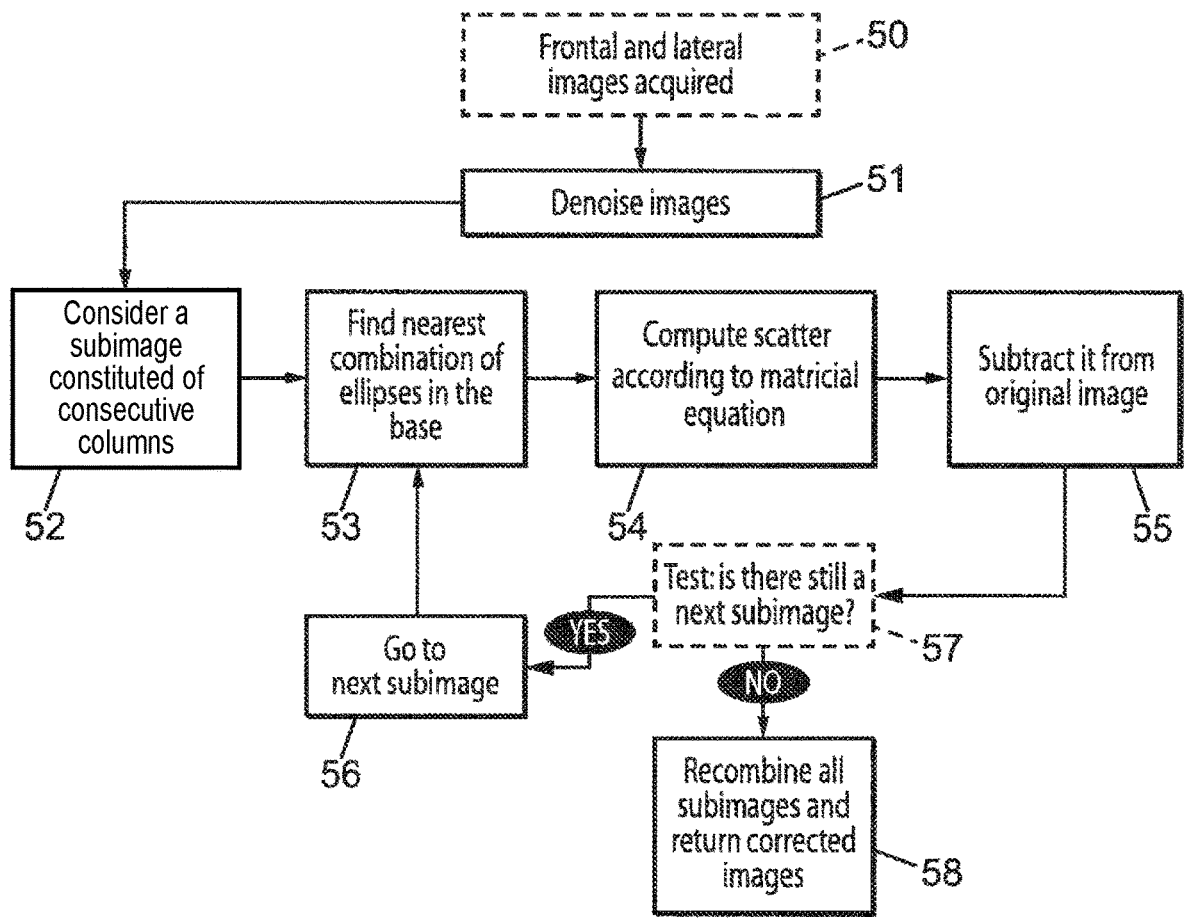
FIG. 8 shows an example of performing the steps of the method of radiography of an organ of a patient according to a second embodiment of the invention, with use of scatter matrix and with scattered signal at same sample rate as compared to direct signal.

FIG. 8 shows an example of performing the steps of the method of radiography of an organ of a patient according to a second embodiment of the invention, with use of scatter matrix and with scattered signal at same sample rate as compared to direct signal.

The different and successive steps of the scatter correction method to correct a given line of pixels on both frontal and lateral views with a preexisting matrix are hereby described.

In a step 50, frontal and lateral images are acquired.

In a step 51, those frontal and lateral images are denoised.

In a step 52, those frontal and lateral images are each divided into sub-images along vertical axis whose height is about 1 cm, representing some consecutive columns of aggregated image.

In a step 53, for each sub-image, the nearest combination of base ellipses within a predetermined family is found.

A scatter matrix is chosen in the matrices database corresponding to the nearest combination of base ellipses. Here the database contains scatter matrices which have the same full resolution as the frontal and lateral raw images, to the contrary of first embodiment in FIG. 6, where those scatter matrices were under-sampled as compared to the frontal and lateral raw images. Either one base ellipse of the family corresponds to concerned sub-image and the corresponding scatter matrix in the database is chosen, or the concerned sub-image corresponds to a linear combination of several ellipses in the family and the linear combination of respective matrices in the database is calculated to give the relevant scatter matrix. Once this scatter matrix is chosen or calculated, the inverse matrix of the scatter matrix is calculated.

In a step 54 an in a step 55, a linear system resolution algorithm, either by using directly the inverse scatter matrix or by using an adapted Richardson-Lucy algorithm previously presented, is applied to compute the direct image given the total image and the inverse scatter matrix (or the scatter matrix), with the same sample rate as the total image. This way, effect of scattering is cancelled from the total image and the obtained direct image is practically free from scattering as if this scattering effect has been subtracted from the total image to give a direct image practically free from scattering, free from cross-scattering as well as free from self-scattering.

In a step 57, either there is yet a next sub-image to be processed and process goes to step 56, or there is no more sub-image to be processed and process goes to step 58.

In a step 56, the next sub-image is processed by getting back to step 53 and by applying it to this next sub-image.

In a step 58, all the sub-images are recombined together to return corrected frontal and lateral images of the patient body. It can be also interesting to use an overlap between sub-images in order to reduce potential artifacts in borders between treated sub-images. This overlap becomes all the more interesting that the size of sub-images becomes bigger.

Figure 9:
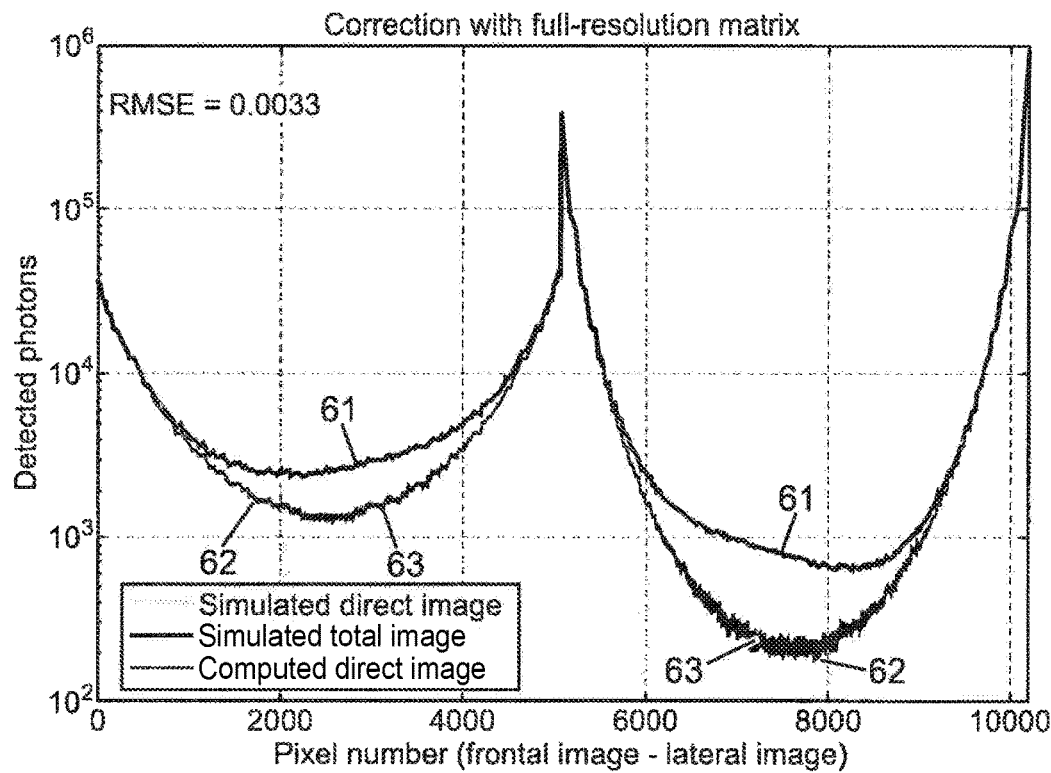
FIG. 9 shows, for all pixels of the image, a comparison between simulated direct image and simulated total image and computed direct image, with matrix representation for received signals on frontal and lateral images, with scattered signal being at same sample rate as compared to direct signal.

FIG. 9 shows, for all pixels of the image, a comparison between simulated direct image and simulated total image and computed direct image, with matrix representation for received signals on frontal and lateral images, with scattered signal being at same sample rate as compared to direct signal.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 µm pixels is corrected with a scatter matrix obtained for 100 µm pixels, indeed with the same sample rate.

The method used in the second embodiment to correct a given clinical image is similar to the method used in the first embodiment, main difference between the sample rate which is here the same for the frontal and lateral raw images on the one hand and for the scatter matrix on the other hand.

The number of detected photons is represented as a function of the position of the pixels, the pixels being numbered from 1 to a bit more than 10000, here in the second embodiment to 10278 as in the first embodiment. The simulated direct image is represented by curve 62, the simulated total image is represented by curve 61, the computed direct image is represented by curve 63.

On FIG. 9, the computed direct signal is well superimposed on the simulated one what is proven by the small Root Mean Square Error (RMSE<0.33%). Indeed, on FIG. 9, curves 62 and 63 are really well superimposed.

The base of matrices consists of a series of water ellipses of clinically-relevant dimensions with 20 mm steps between consecutive ellipse axis dimensions, placed in different positions: rotation steps at −20°, 0 and 20° and a translation grid from −125 to 125 mm in both directions with steps of 25 mm. The resulting matrices can be combined to obtain the best matrix for a given image slice. The choice of the best parameters will be automated based on the images obtained through the simulations of realistic 3D generic models.

Figure 10:
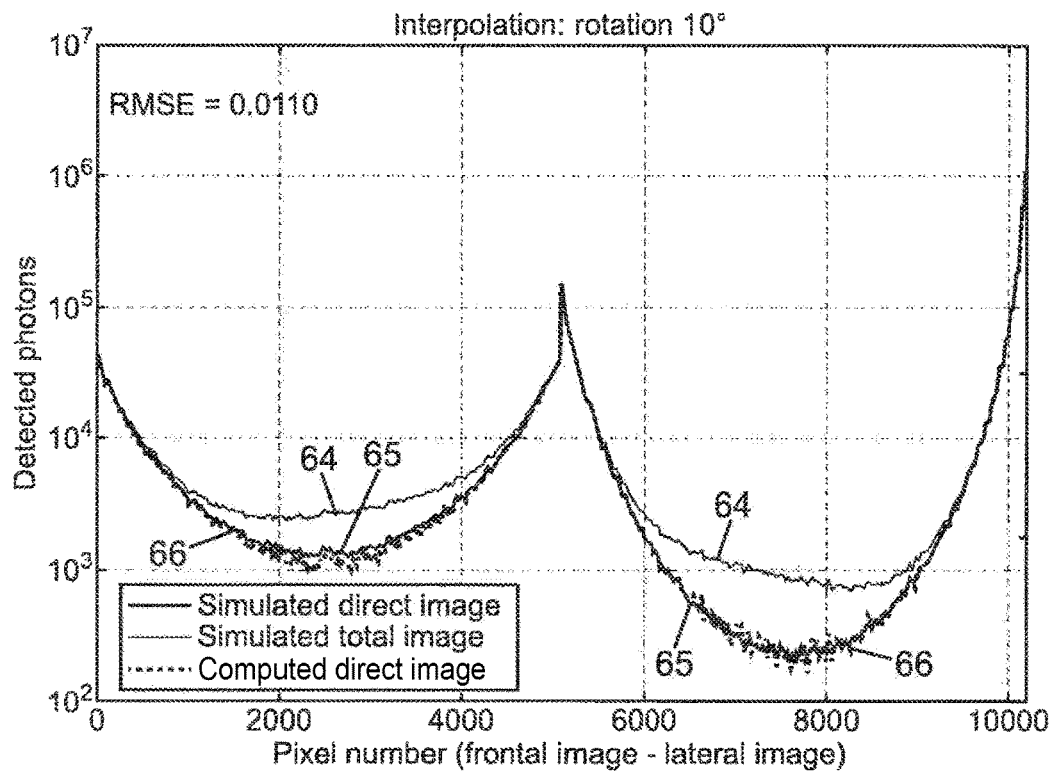
FIG. 10 shows, for all pixels of the image, a comparison between simulated direct image and simulated total image and computed direct image, with matrix representation for received signals on frontal and lateral images, with scattered signal being under-sampled as compared to direct signal, for an interpolation for a rotation of the patient specific modeling between two predetermined orientations.
Figure 11:
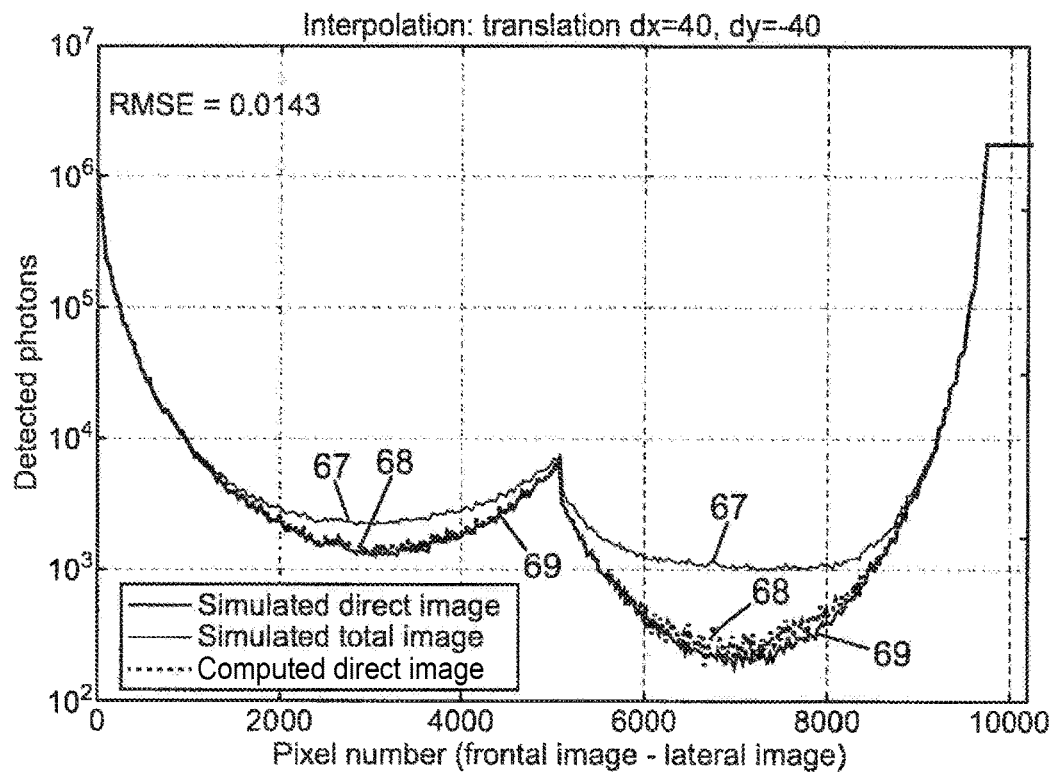
FIG. 11 shows, for all pixels of the image, a comparison between simulated direct image and simulated total image and computed direct image, with matrix representation for received signals on frontal and lateral images, with scattered signal being under-sampled as compared to direct signal, for an interpolation for a translation of the patient specific modeling between four predetermined positions.
Figure 12:
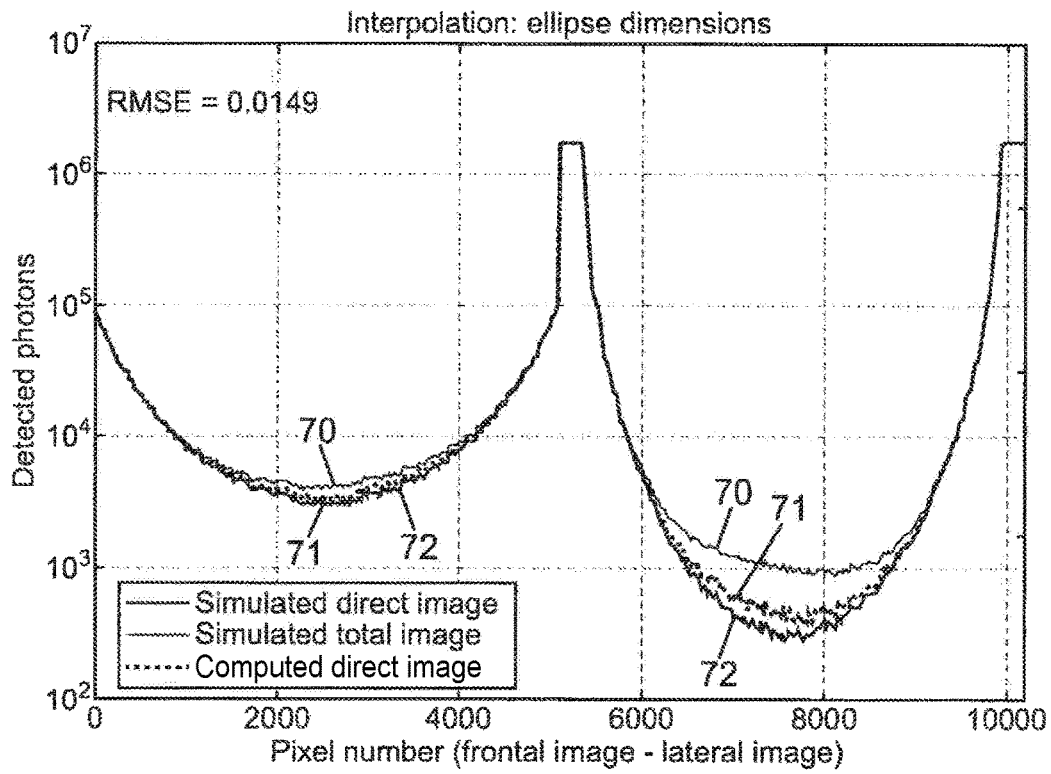
FIG. 12 shows, for all pixels of the image, a comparison between simulated direct image and simulated total image and computed direct image, with matrix representation for received signals on frontal and lateral images, with scattered signal being under-sampled as compared to direct signal, for an intermediate dimension of the patient specific modeling between two predetermined ellipses sizes.

The steps were chosen to assure a correction with a logarithmic root mean square error smaller than 5% for reference cases, i.e. using water ellipses. FIGS. 10 to 12 show results of these approximations.

FIG. 10 shows, for all pixels of the image, a comparison between simulated direct image and simulated total image and computed direct image, with matrix representation for received signals on frontal and lateral images, with scattered signal being under-sampled as compared to direct signal, for an interpolation for a rotation of the patient specific modeling between two predetermined orientations.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 µm pixels is corrected with a scatter matrix obtained for 2 mm large pixels, indeed with an under-sampling factor of 20. An interpolation between matrices corresponding respectively to orientation of 0° of angular rotation (patient facing the frontal source) and orientation of 20° angular rotation (patient rotated of 20° with respect to frontal source) is made to assess the validity of the approximation made by computing as compared to simulation for an angular rotation of 10° (patient rotated of 10° with respect to frontal source).

The number of detected photons is represented as a function of the position of the pixels, the pixels being numbered from 1 to 10200. The simulated direct image is represented by curve 65, the simulated total image is represented by curve 64, the computed direct image is represented by curve 66.

On FIG. 10, the computed direct signal is well superimposed on the simulated one what is proven by the small Root Mean Square Error (RMSE<1.1%). Indeed, on FIG. 10, curves 65 and 66 are rather well superimposed.

FIG. 11 shows, for all pixels of the image, a comparison between simulated direct image and simulated total image and computed direct image, with matrix representation for received signals on frontal and lateral images, with scattered signal being under-sampled as compared to direct signal, for an interpolation for a translation of the patient specific modeling between four predetermined positions.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 μm pixels is corrected with a scatter matrix obtained for 2 mm large pixels, indeed with an under-sampling factor of 20. An interpolation between matrices corresponding respectively to position of [25,−25] (patient shifted by 25 mm towards the rear of frontal source and by 25 mm towards the front of lateral source) and to position of [25,−50] (patient shifted by 25 mm towards the rear of frontal source and by 50 mm towards the front of lateral source) and to position of [50,−25] (patient shifted by 50 mm towards the rear of frontal source and by 25 mm towards the front of lateral source) and to position of [50,−50] (patient shifted by 50 mm towards the rear of frontal source and by 50 mm towards the front of lateral source) is made to assess the validity of the approximation made by computing as compared to simulation for a position of Δx=40 mm and of Δy=−40 mm (patient shifted by 40 mm towards the rear of frontal source and by 40 mm towards the front of lateral source).

The number of detected photons is represented as a function of the position of the pixels, the pixels being numbered from 1 to 10200. The simulated direct image is represented by curve 69, the simulated total image is represented by curve 67, the computed direct image is represented by curve 68.

On FIG. 11, the computed direct signal is well superimposed on the simulated one what is proven by the small Root Mean Square Error (RMSE<1.5%). Indeed, on FIG. 11, curves 68 and 69 are rather well superimposed.

FIG. 12 shows, for all pixels of the image, a comparison between simulated direct image and simulated total image and computed direct image, with matrix representation for received signals on frontal and lateral images, with scattered signal being under-sampled as compared to direct signal, for an intermediate dimension of the patient specific modeling between two predetermined ellipses sizes.

Here the patient body is simulated by a water elliptic tube presenting a cross section with axes of 420 mm and of 310 mm which is not an ellipse contained in the family. But an interpolation is made between two ellipses contained in the family, which are respectively an ellipse of dimensions 420 mm by 290 mm (meaning presenting a cross section with axes of 420 mm and of 290 mm) and an ellipse of dimensions 400 mm by 310 mm, in order to to assess the validity of the approximation made by computing as compared to simulation for this interpolated ellipse. There are 60 keV monochromatic sources, a detector height of 3.2 mm, a collimation airgap of 50 mm. The received signal on detectors presenting 100 μm pixels is corrected with a scatter matrix obtained for 2 mm large pixels, indeed with an under-sampling factor of 20.

The number of detected photons is represented as a function of the position of the pixels, the pixels being numbered from 1 to 10200. The simulated direct image is represented by curve 72, the simulated total image is represented by curve 70, the computed direct image is represented by curve 71.

On FIG. 12, the computed direct signal is well superimposed on the simulated one what is proven by the small Root Mean Square Error (RMSE<1.5%). Indeed, on FIG. 12, curves 71 and 72 are rather well superimposed.

Figure 13A:
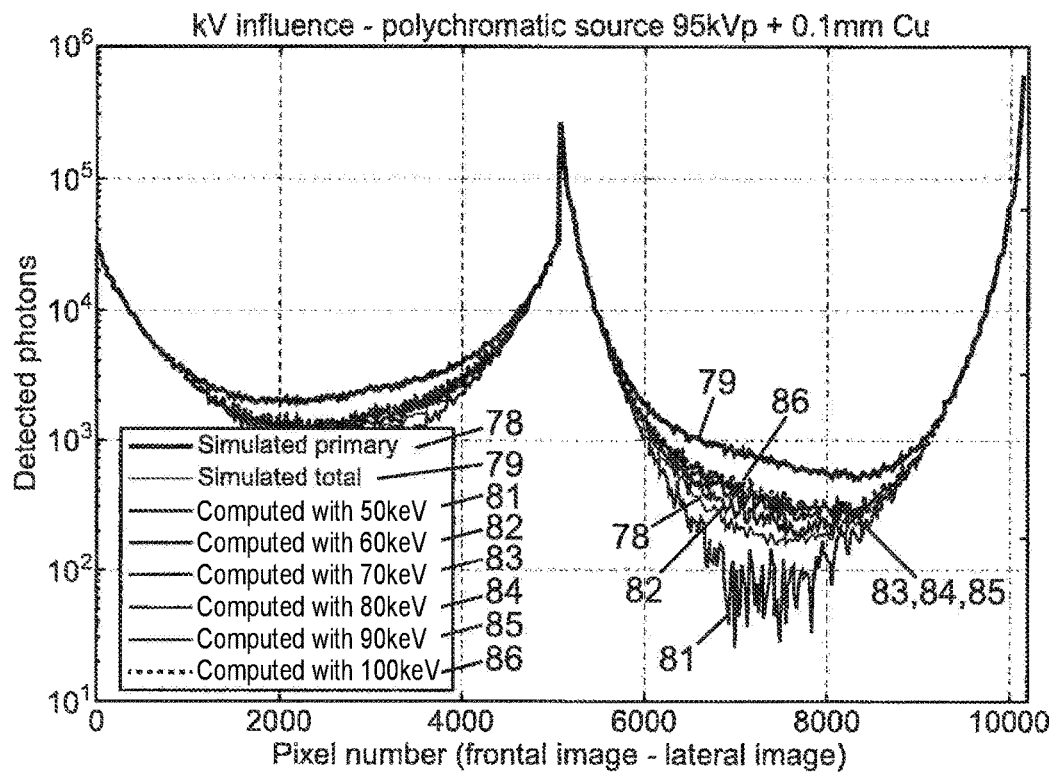
Figure 13B:
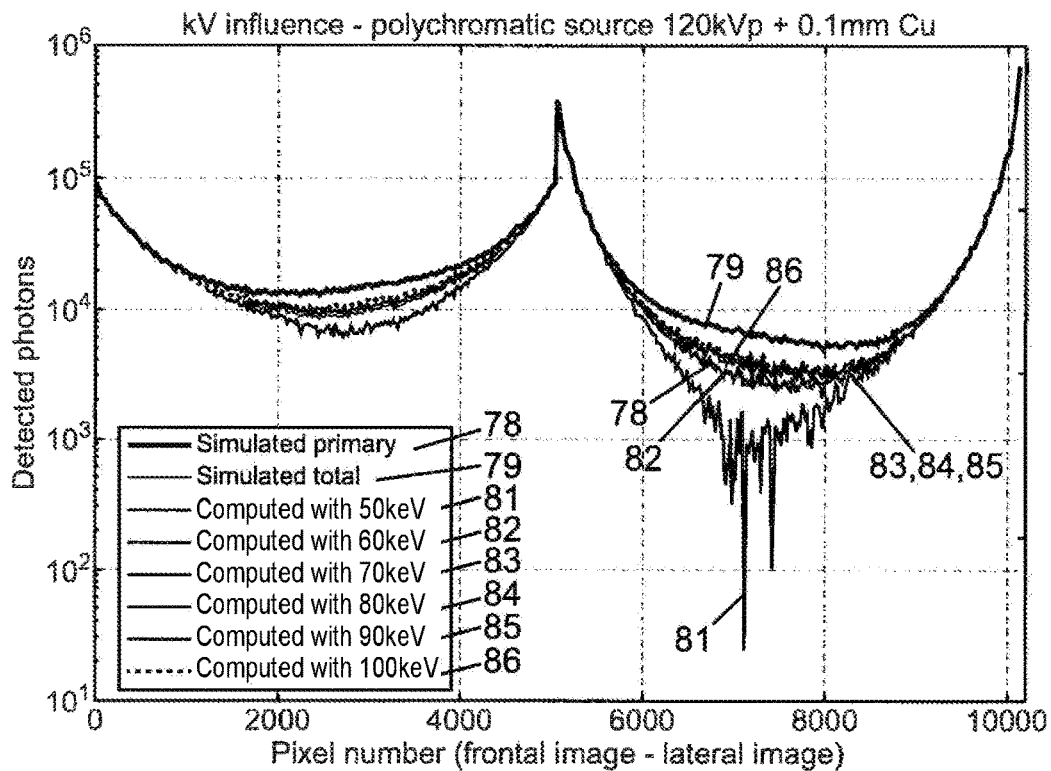

FIGS. 13a, 13b and 13c, show, for all pixels of the image, a comparison between different X-ray spectra of radiation sources used to determine radiation scattering, in order to evaluate best range of X-ray spectrum of radiation sources to be used to determine radiation scattering.

Here the patient body is simulated by a water elliptic tube presenting a cross section with axes of 440 mm and of 350 mm. There are a detector height of 3.2 mm and a collimation airgap of 50 mm. The received signal on detectors presenting 100 μm pixels is corrected with a scatter matrix obtained for 2 mm large pixels, indeed with an under-sampling factor of 20.

Several scatter matrices for a same ellipse have been computed with monchromatic frontal and lateral sources, respectively of different energies which are 50 keV, 60 keV, 70 keV, 80 keV, 90 keV and 100 keV.

The simulated direct image is represented by curve 78, the simulated total image is represented by curve 79, the computed direct image is represented respectively by curve 81 for monochromatic sources of 50 keV energy, by curve 82 for monochromatic sources of 60 keV energy, by curve 83 for monochromatic sources of 70 keV energy, by curve 84 for monochromatic sources of 80 keV energy, by curve 85 for monochromatic sources of 90 keV energy, by curve 86 for monochromatic sources of 100 keV energy. It can be seen that the scatter matrix dependence of the level of energy of the monochromatic sources used to compute this scatter matrix, first is not very strong, and second leads to all curves 81 to 86 either being rather well superimposed on curve 78 of simulated direct image or at least being close to this curve 78 of simulated direct image.

In FIG. 13a, the radiation sources used to simulate the raw images are polychromatic sources having a tube voltage of 95 kV with 0.1 mm copper (Cu) additional filtration.

In FIG. 13b, the radiation sources used to simulate the raw images are polychromatic sources having a tube voltage of 120 kV with 0.1 mm copper (Cu) additional filtration.

In FIG. 13c, represents a table giving the RMSE for each matricial computation with reference to simulated direct image. It can be seen on this table that, either for the first case of the polychromatic sources having a tube voltage of 95 keVp with 0.1 mm copper filtration or for the second case of polychromatic sources having a tube voltage of 120 keVp with 0.1 mm copper (Cu) filtration, there is an optimal low RMSE for a value of the energy of the monochromatic sources used to compute the scatter matrix which is 60 keV. This optimal value of the energy of the monochromatic sources used to compute the scatter matrix will be chosen, accordingly to a preferred embodiment of the invention at 60 keV.

FIGS. 14a and 14b show, for all pixels of the image, a comparison between simulated direct image and simulated total image and computed direct image, with matrix representation for received signals on frontal and lateral images, with scattered signal being under-sampled as compared to direct signal, showing the effect of bone and air inclusions.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 μm pixels is corrected with a scatter matrix obtained for 2 mm large pixels, indeed with an under-sampling factor of 20. The simulated ellipses modeling the patient can be used as homogeneously composed of water, but can also be used, if needed, to correct highly heterogeneous slices containing not only water (or soft tissues) but also bone inclusions and air bubbles to give more realistic and more accurate results in the computed scatter matrix.

On FIG. 14a, it can be seen that, inside the water elliptic tube 87, there are a bone inclusion 88 presenting a diameter of 50 mm and an air inclusion 89 presenting a diameter of 25 mm. FIG. 14a represents a slice of the phantom used to compute the scatter matrix. It can be seen that the elliptic tube presents a 0° orientation with respect to frontal detector. A scale representing density is located on the right of FIG. 14a. it can be seen that the water elliptic tube 87 presents a density value of roughly 1, whereas the bone inclusion 88 presents a densisty value of roughly 2, and whereas the air inclusion 89 presents a densisty value of roughly 0. Values given along abscisse axis and ordonate axis are distances in mm with respect to the center of the water elliptic tube 87.

On FIG. 14b, the number of detected photons is represented as a function of the position of the pixels, the pixels being numbered from 1 to 10200. The simulated direct image is represented by curve 91, the simulated total image is represented by curve 90, the computed direct image is represented by curve 92. The computed direct signal is rather well superimposed on the simulated one what is proven by the small Root Mean Square Error (RMSE<2.5%). Indeed, on FIG. 14b, curves 91 and 92 are rather well superimposed.

Figure 15A:
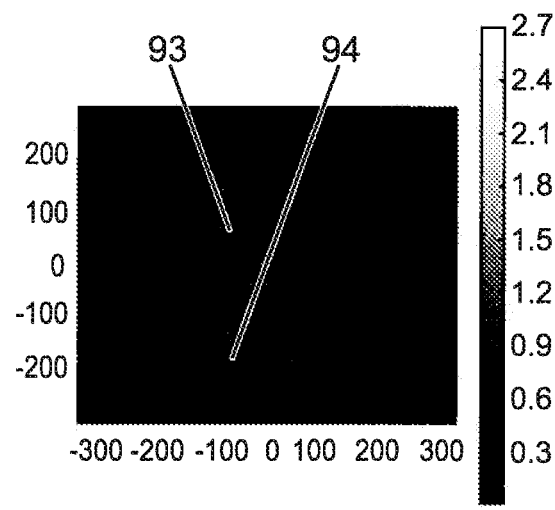
FIGS. 15a and 15b show, for all pixels of the image, a comparison between simulated direct image and simulated total image and computed total image, with matrix representation for received signals on frontal and lateral images, with scattered signal being under-sampled as compared to direct signal, showing the effect of a more complex structure of the ellipse including water cylinder surrounded by adipose tissue.
Figure 15B:
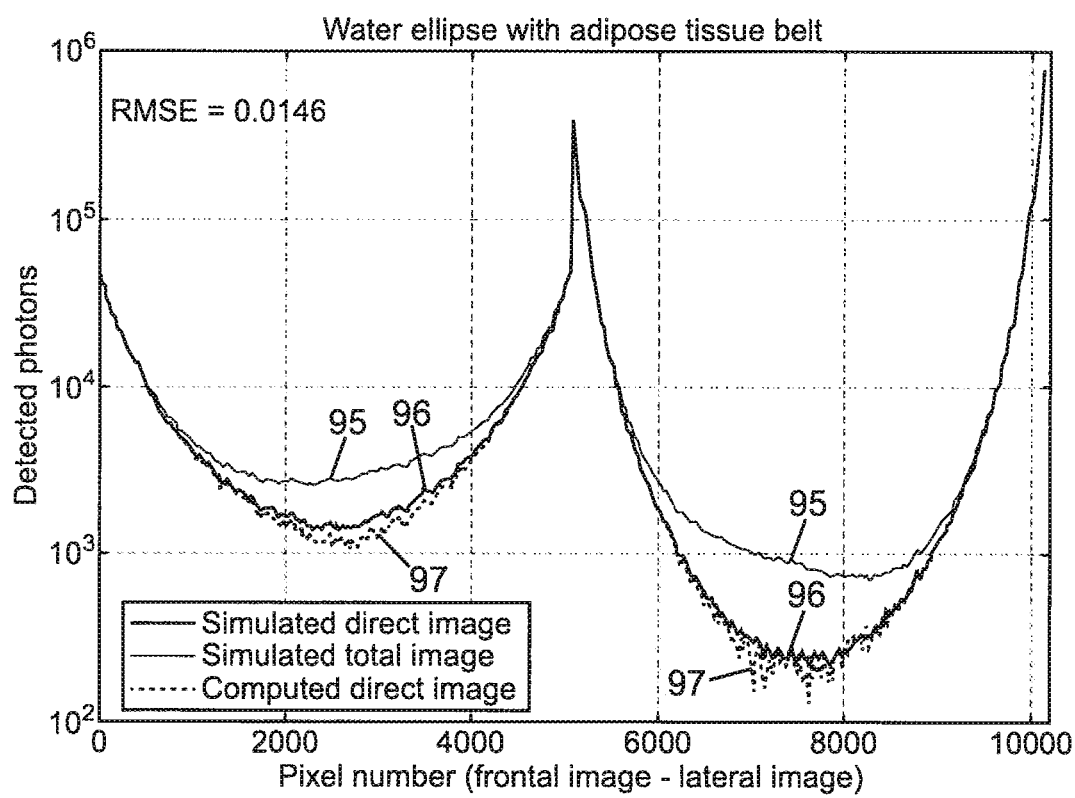

FIGS. 15a and 15b show, for all pixels of the image, a comparison between simulated direct image and simulated total image and computed total image, with matrix representation for received signals on frontal and lateral images, with scattered signal being under-sampled as compared to direct signal, showing the effect of a more complex structure of the ellipse including water cylinder surrounded by adipose tissue.

Here the patient body is simulated by a water elliptic tube presenting a cross section with axes of 440 mm and of 350 mm. There are 60 keV monochromatic sources, a detector height of 3.2 mm, a collimation airgap of 50 mm. The received signal on detectors presenting 100 µm pixels is corrected with a scatter matrix obtained for 2 mm large pixels, indeed with an under-sampling factor of 20. The simulated ellipses modeling the patient can be used as homogeneously composed of water, but can also be used, if needed, to correct somewhat heterogeneous slices containing not only water (or flesh soft tissues) but also an outer ring of adipose tissue (of lower density than water) to give more realistic and more accurate results in the computed scatter matrix, especially in case of obese patients. Indeed, obese patients have a high level of fat here modelised by a water cylinder surrounded by an adipose tissue belt.

On FIG. 15a, it can be seen that, the water elliptic tube 93 is surrounded by a ring of adipose tissue 94 of about 20 mm thickness, thereby giving a very realistic representation of an overweight or obese patient. FIG. 15a represents a slice of the phantom used to compute the scatter matrix. It can be seen that the elliptic tube presents a 0° orientation with respect to frontal detector. A scale representing density is located on the right of FIG. 15a. it can be seen that the water elliptic tube 93 presents a density value of roughly 1, whereas the outer ring of adipose tissue presents a densisty value of roughly 0.9. Values given along abscisse axis and ordonate axis are distances in mm with respect to the center of the water elliptic tube 93.

On FIG. 15b, the number of detected photons is represented as a function of the position of the pixels, the pixels being numbered from 1 to 10200. The simulated direct image is represented by curve 96, the simulated total image is represented by curve 95, the computed direct image is represented by curve 97. The computed direct signal is rather well superimposed on the simulated one what is proven by the small Root Mean Square Error (RMSE<1.5%). Indeed, on FIG. 15b, curves 96 and 97 are rather well superimposed.

Figure 16A:
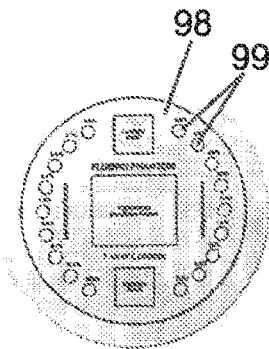
FIGS. 16a, 16b and 16c, show performing, on different spots, a comparison between different raw images and different processed images, with respect to the peak signal to noise ratio.
Figure 16B:
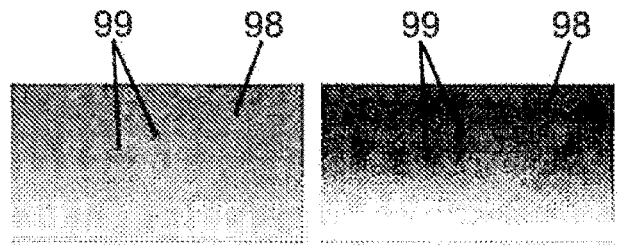
Figure 16C:
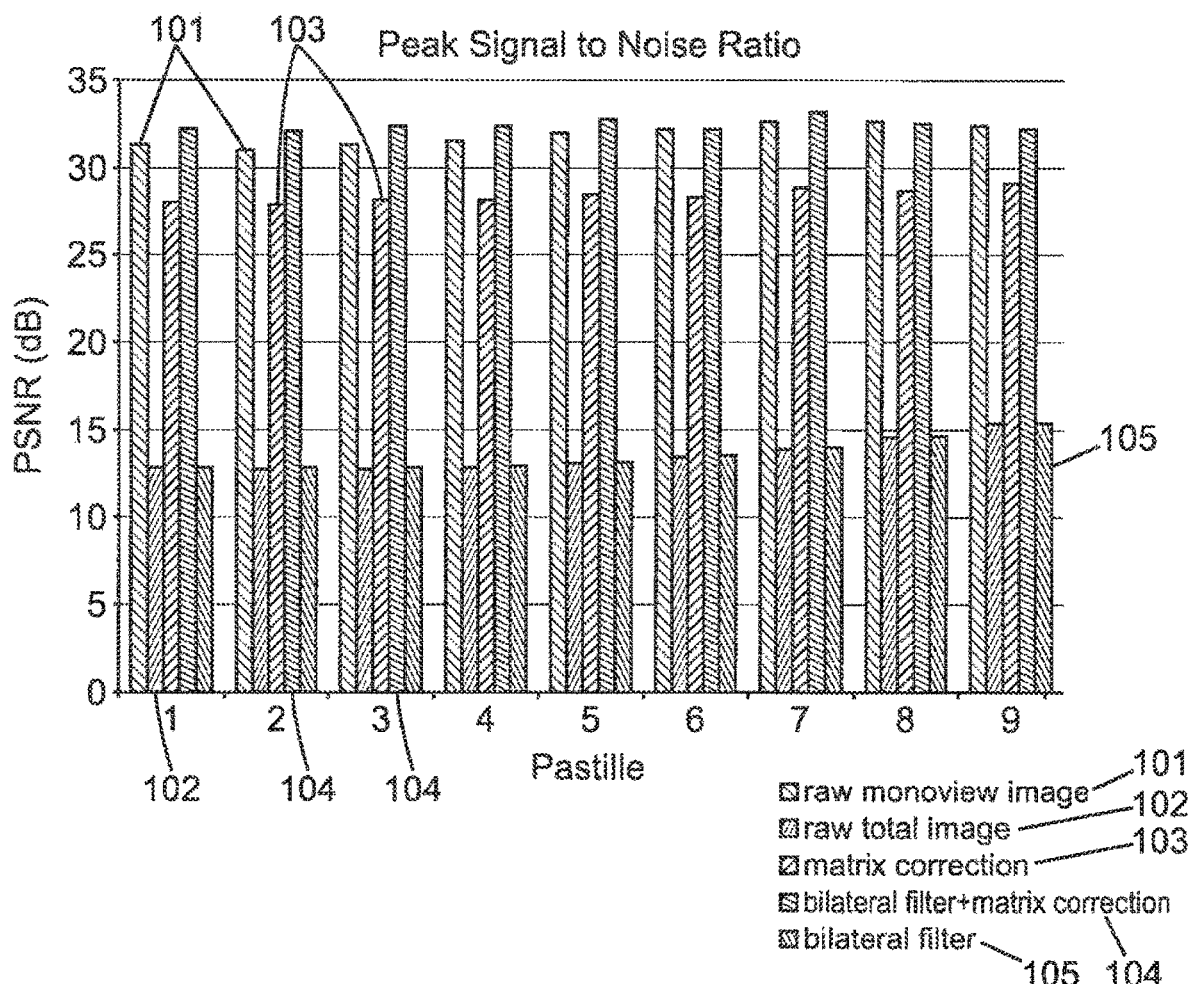

FIGS. 16a, 16b and 16c, show performing, on different spots, a comparison between different raw images and different processed images, with respect to the peak signal to noise ratio.

This scatter reduction method according to embodiments of the invention enhances image quality, as will be proved with a PHD 5000 fluoro-phantom placed in a 400 mm diameter water cylinder with a detector height of 6.4 mm and with a collimation air gap of 50 mm, with polychromatic sources having a tube voltage of 120 kV with a 0.1 mm copper filtration.

FIG. 16a gives a picture of a PHD5000 fluoro phantom 98 containing contrast spots 99.

FIG. 16b gives simulated images of the contrast spots 99 of the phantom 98. On the left of FIG. 16b, there is the total image, including both direct signal and scattering (self-scattering and cross-scattering signals), whereas on the right of FIG. 16b, there is the denoised and corrected image where it can be seen that the spots 99 are much more easily detected on the corrected image than on the raw total image.

FIG. 16c gives, for several different spots 99 numbered 1 to 9, the PSNR (Peak Signal to Noise Ratio) of several different images including each time five cases. FIG. 16c shows an histogram with several bars for each spot, one bar per case. Those five cases are: first case corresponding to a raw monoview image (including direct and self-scattered signals) and represented by bar 101; second case corresponding to a raw total image (including direct and self-scattererd and cross-scattered signals) and represented by bar 102; third case corresponding to a correction by a scatter matrix (so as to get a corrected signal which is a computed direct signal) and represented by bar 103; fourth case corresponding to a double correction integrating both a denoising correction with a bilateral filter and a correction by a scatter matrix (so as to get denoised and corrected signal which is a computed direct signal) and represented by bar 104; fifth case corresponding to a denoising correction with a bilateral filter (so as to get a denoised total image) and represented by bar 105.

The total image, 75% to 90% of it being either cross-scattering or self-scattering, was denoised and corrected. This results in a clear improvement of Peak Signal to Noise Ratio on each of the nine spots as can be seen on FIG. 16c. The Peak Signal to Noise Ratio is given by following equation:

$$PSNR(I_{ref}, I) = 10 \log_{10} \frac{d^2}{MSE(I_{ref}, I)} \text{ where } d = 2^{16}$$

(the dynamic range of the image) and $MSE(I_{ref}, I) = E((I_{ref} - I)^2)$ and $I_{ref}$ being the simulated direct signal presenting no scattering, E being the expected value or the mean value.

First case corresponding to a raw monoview image and represented by bar 101 is a reference of good level which would be very satisfactory. Raw monoview image has no cross-scattering but has self-scattering representing about 10-15% of the whole amount of scattering. Second case corresponding to a raw total image and represented by bar 102 is the reference of bad level to be improved. Third case corresponding to a correction by a scatter matrix and represented by bar 103 already gives a good result showing how efficient is this scatter matrix correction, since bar 103 is nearly as high as bar 101 (reference of good level) and anyway much higher than bar 102 (reference of bad level). Fourth case corresponding to a double correction integrating both a denoising correction with a bilateral filter and a correction by a scatter matrix and represented by bar 104 gives a very good and optimized level, since bar 104 is even higher than bar 101 (reference of good level) and anyway much higher than bar 102 (reference of bad level). Fifth case corresponding to only a denoising correction with a bilateral filter and represented by bar 105 gives a result which remains similar to the raw total image (reference of bad level) showing that denoising alone is clearly insufficient, since bars 105 and 102 present comparable relative heights.

As a summary: "denoising alone" is not only very unsufficient to improve raw total image quality, but also brings practically no quality improvement; "scatter matrix correction" alone is not only good to improve raw total image quality, but also reaches not far from good reference level of raw monoview image devoid of cross-scattering; both "denoising alone" and "scatter matrix correction" are not only very good to improve raw total image quality, but also reach together an even better result than good reference level of raw monoview image devoid of cross-scattering, thereby showing that whereas "denoising alone" has little effect on raw image quality improvement, combination of "denoising" with "scatter matrix correction" notably improves even over "scatter matrix correction alone" which was already good.

Figure 17A:
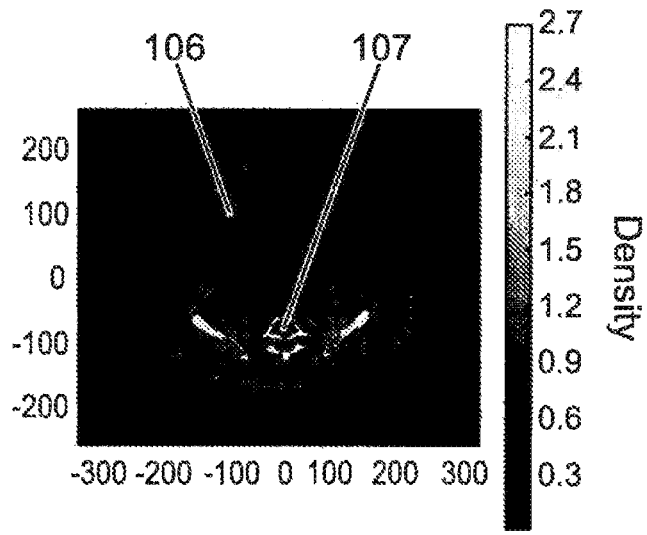
FIGS. 17a, 17b and 17c, show performing, on different patient specific modelings, a comparison between different raw images and different processed images, with respect to the peak signal to noise ratio, with matrix representation for received signals on frontal and lateral images.
Figure 17B:
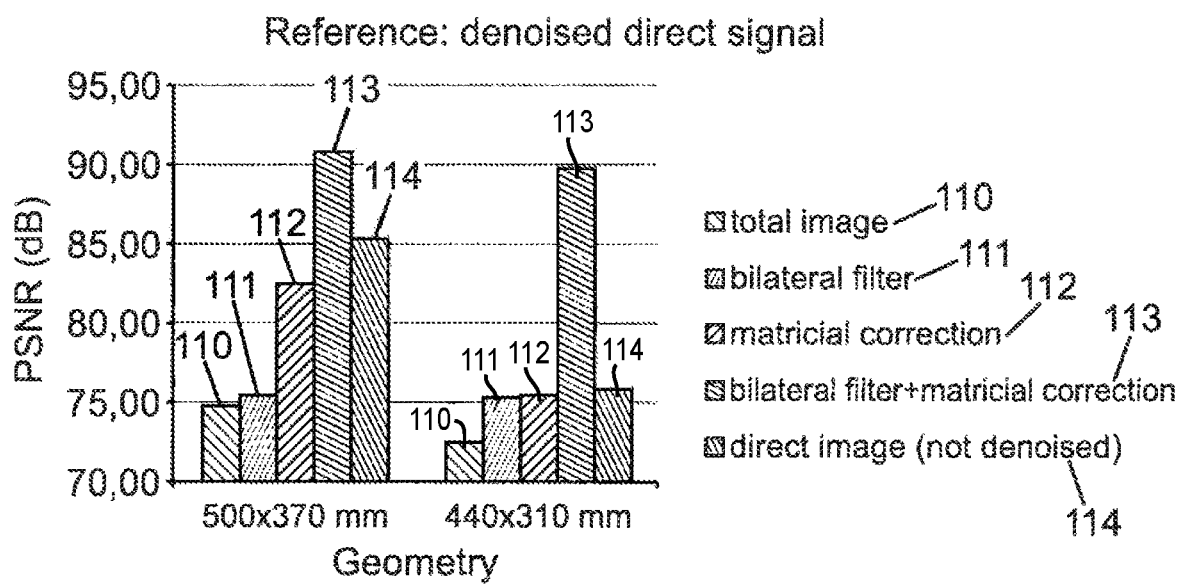
Figure 17C:
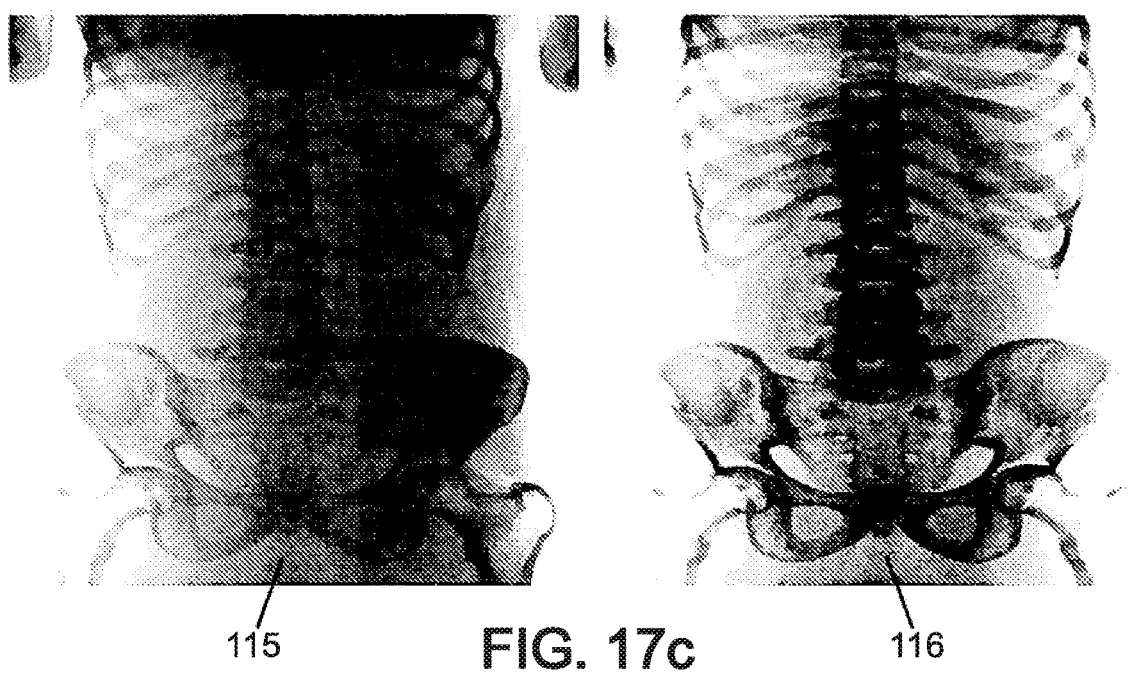

FIGS. 17a, 17b and 17c, show performing, on different patient specific modelings, a comparison between different raw images and different processed images, with respect to the peak signal to noise ratio, with matrix representation for received signals on frontal and lateral images.

In FIG. 17a, a thin human phantom 107 has been surrounded by a water cylinder 106 to increase scatter signal. FIG. 17a corresponds to more realistic cases simulations than the spots of FIG. 16a. A thin human phantom model 107 was surrounded by a first water cylinder 106 (axes of 500 and 370 mm) and then by a second water cylinder (of axes of 440 and 310 mm) in order to force a high proportion of scatter in the raw images, for instance here from 60% to 90% of signal in raw images is due to scattering signal.

Here the patient body is simulated successively by two different water elliptic tubes 106 surrounding two identical thin phantoms 107, first water elliptic tube presenting a cross section with axes of 500 mm and of 370 mm, second water elliptic tube presenting a cross section with axes of 440 mm and of 310 mm. There are 60 keV monochromatic sources, a detector height of 3.2 mm, a collimation airgap of 50 mm. The received signal on detectors presenting 100 µm pixels is corrected with a scatter matrix obtained for 2 mm large pixels, indeed with an under-sampling factor of 20.

FIG. 17a represents a slice of the phantom (thin human phantom surrounded by water elliptic tube) used to compute the scatter matrix. It can be seen that the elliptic tube presents a 0° orientation with respect to frontal detector. A scale representing density is located on the right of FIG. 17a. It can be seen that the water elliptic tube 106 presents a density value of roughly 1, whereas the thin human phantom presents a densisty value between 1 and 2. Values given along abscisse axis and ordonate axis are distances in mm with respect to the center of the water elliptic tube 106.

FIG. 17b gives, for both previously presented water elliptic tubes 106, the PSNR (Peak Signal to Noise Ratio) of several different images including each time five cases. FIG. 17b shows an histogram with several bars, one bar per case. Those five cases are: first case corresponding to a raw total image (including direct and self-scattered and cross-scattered signals) and represented by bar 110; second case corresponding to a denoising correction with a bilateral filter (so as to get a denoised total image) and represented by bar 111; third case corresponding to a correction by a scatter matrix (so as to get a corrected signal which is a computed direct signal) and represented by bar 112; fourth case corresponding to a double correction integrating both a denoising correction with a bilateral filter and a correction by a scatter matrix (so as to get denoised and corrected signal which is a computed direct signal) and represented by bar 113; fifth case corresponding to a raw monoview image (including direct and self-scattered signals) and represented by bar 114.

Now, the different cases corresponding to bars 110 to 114 will be compared to one another, for the thin human phantom surrounded by the water elliptic tube of axes 500 mm and 370 mm, simulating an obese patient. Fifth case corresponding to a raw monoview image and represented by bar 114 is a reference of good level which would be very satisfactory. Raw monoview image has no cross-scattering but has self-scattering representing about 10-15% of the whole amount of scattering. First case corresponding to a raw total image and represented by bar 110 is the reference of bad level to be improved. Third case corresponding to a correction by a scatter matrix and represented by bar 112 already gives a good result showing how efficient is this scatter matrix correction, since bar 112 is nearly as high as bar 114 (reference of good level) and anyway much higher than bar 110 (reference of bad level). Fourth case corresponding to a double correction integrating both a denoising correction with a bilateral filter and a correction by a scatter matrix and represented by bar 113 gives a very good and optimized level, since bar 113 is even higher than bar 114 (reference of good level) and anyway much higher than bar 110 (reference of bad level). Second case corresponding to only a denoising correction with a bilateral filter and represented by bar 111 gives a result which remains similar to the raw total image (reference of bad level) showing that denoising alone is clearly insufficient, since bars 110 and 111 present comparable relative heights.

As a summary, for an obese patient: "denoising alone" is not only very unsufficient to improve raw total image quality, but also brings practically no quality improvement; "scatter matrix correction" alone is not only good to improve raw total image quality, but also reaches not far from good reference level of raw monoview image devoid of cross-scattering; both "denoising alone" and "scatter matrix correction" are not only very good to improve raw total image quality, but also reach together an even better result than good reference level of raw monoview image devoid of cross-scattering, thereby showing that whereas "denoising alone" has little effect on raw image quality improvement, combination of "denoising" with "scatter matrix correction" notably improves even over "scatter matrix correction alone" which was already good.

Now, the different cases corresponding to bars 110 to 114 will be compared to one another, for the thin human phantom surrounded by the water elliptic tube of axes 440 mm and 310 mm, simulating an overweight patient. Fifth case corresponding to a raw monoview image and represented by bar 114 is a reference of rather good level which would be quite satisfactory. Raw monoview image has no cross-scattering but has self-scattering representing about 10-15% of the whole amount of scattering. First case corresponding to a raw total image and represented by bar 110 is the reference of bad level to be improved. Third case corresponding to a correction by a scatter matrix and represented by bar 112 already gives a correct result, since bar 112 is nearly as high as bar 114 (reference of rather good level) and anyway notably higher than bar 110 (reference of bad level). Fourth case corresponding to a double correction integrating both a denoising correction with a bilateral filter and a correction by a scatter matrix and represented by bar 113 gives a very good and optimized level, since bar 113 is even notably higher than bar 114 (reference of rather good level) and anyway much higher than bar 110 (reference of bad level). Second case corresponding to only a denoising correction with a bilateral filter and represented by bar 111 gives a result which improves over the raw total image (reference of bad level) in a comparable way to the improvement peformed by correction by a scatter matrix alone, since bars 111 and 112 present comparable relative heights.

As a summary, for an overweight patient: "denoising alone" brings correct improvement on image quality; "scatter matrix correction" alone brings a comparable correct improvement on image quality; both "denoising alone" and "scatter matrix correction" are not only very good to improve raw total image quality, but also reach together an even notably better result than good reference level of raw monoview image devoid of cross-scattering.

FIG. 17c gives simulated images of the the water elliptic tube presenting axes of 500 mm and of 370 mm, corresponding to simulation of an obese patient, surrounding the thin human phantom. On the left of FIG. 17c, there is the total image, including both direct signal and scattering (self-scattering and cross-scattering signals), whereas on the right of FIG. 17c, there is the denoised and corrected image where it can be seen that the different bones (ribs, spine, . . . ) are notably more easily detected on the corrected image than on the raw total image. It can be seen that the scatter is highly dissymetric, adding a large gradient of scatter signal, much more on right than on left of patient image.

Figure 18:
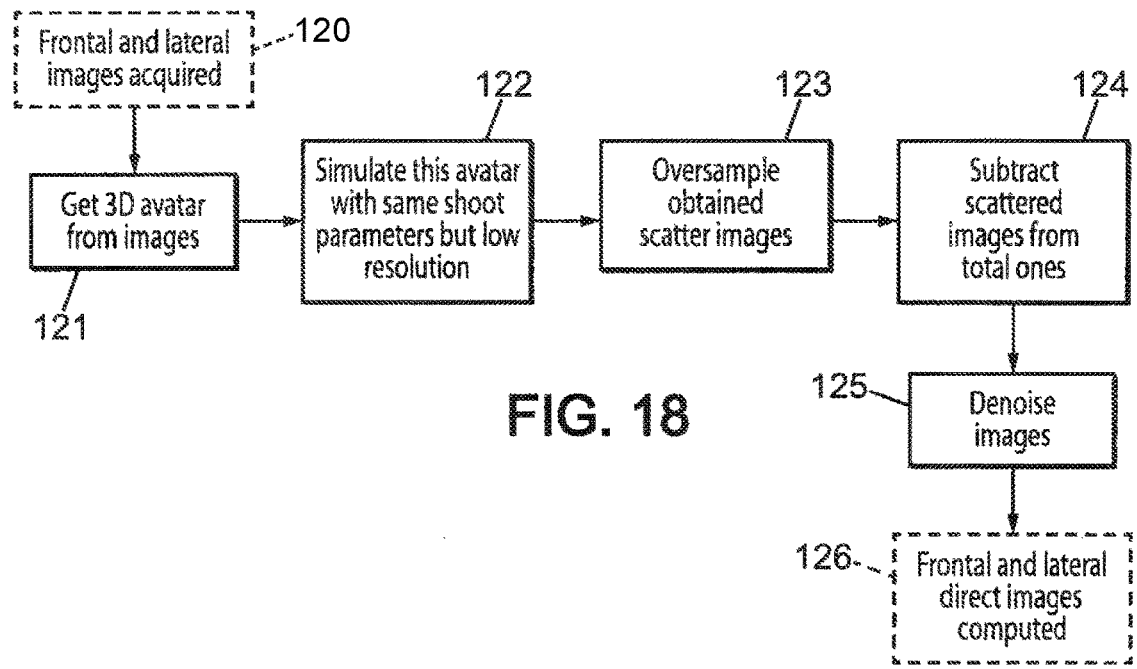
FIG. 18 shows an example of performing the steps of the method of radiography of an organ of a patient according to a third embodiment of the invention, with use of 3D avatar for patient specific modeling.

FIG. 18 shows an example of performing the steps of the method of radiography of an organ of a patient according to a third embodiment of the invention, with use of 3D avatar for patient specific modeling and with scattered signal being under-sampled as compared to direct signal.

The different and successive steps of the scatter correction method to correct a given line of pixels on both frontal and lateral views with a preexisting generic model of a patient are hereby described. This predetermined generic model is preferably common to all patients. If there is a predetermined set of generic models, there will be an additional preliminary step of choosing the most adapted generic model with respect to the patient corpulence.

In a step 120, frontal and lateral images are acquired.

In a step 121, a 3D (three dimensional) avatar is got both from the chosen generic model and from those raw frontal and lateral images. The raw frontal and lateral images are used to modify the generic model and to adapt it to the patient so that this got 3D avatar is a 3D representation representative of the patient morphology.

In a step 122, this effect of scattering, including cross-scattering and also preferably self-scattering, is simulated on this 3D avatar with the same shoot parameters as the shoot parameters used to make the raw frontal and lateral images, but for a lower resolution so as to reduce computing time, so as to get frontal and lateral under-sampled scatter images which are respectively representative of scattering effect on frontal and lateral images.

In an alternative step 122, this effect of scattering, cross-scattering and also preferably self-scattering, is simulated on this 3D avatar with the same shoot parameters as the shoot parameters used to make the raw frontal and lateral images, as well as the same resolution, so as to get frontal and lateral scatter images which are respectively representative of scattering effect on frontal and lateral images, with the same resolution and the same sample rate as the frontal and lateral raw images. Then, the step 123 would be bypassed. This may be somewhat more precise, but at the cost of a very important computing time increase. This alternative step 122 is possible, but is not preferred.

In a step 123, the frontal and lateral under-sampled scatter images are over-sampled by linear interpolation and the resulting images are smoothed so as to get the frontal and lateral oversampled scatter images, which now have the same sample rate as the frontal and lateral raw images.

In a step 124, these frontal and lateral oversampled scatter images are subtracted from the frontal and lateral raw images, which are total images i.e. images including direct signal as well as scattered signal, so as to get frontal and lateral intermediate images.

In a step 125, those frontal and lateral intermediate images are denoised so as to get frontal and lateral computed direct images.

In a step 126, those frontal and lateral computed direct images can be displayed or printed.

Figure 19:
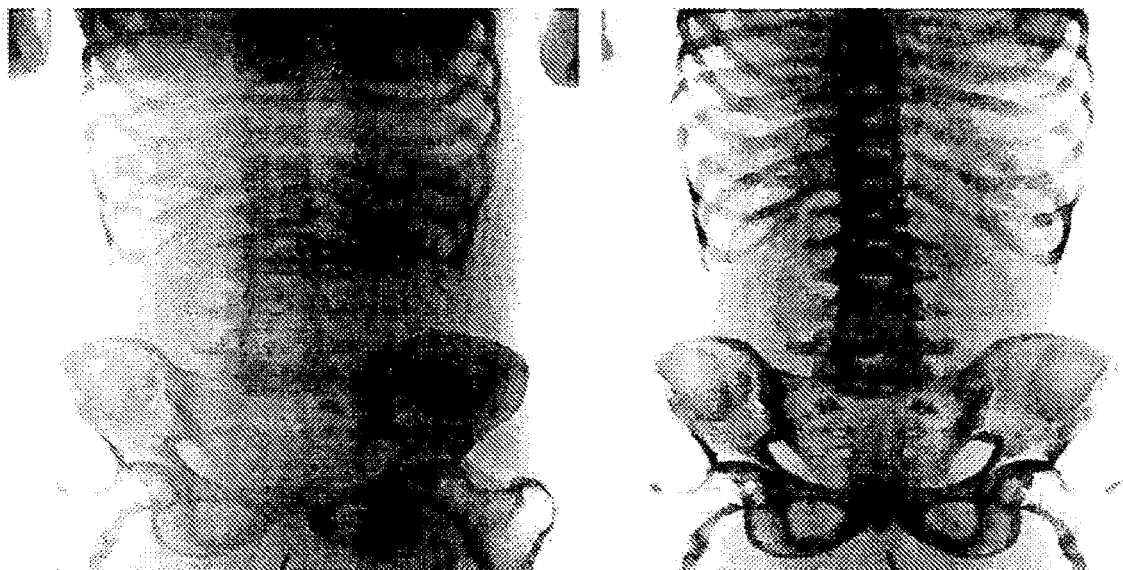
FIG. 19 shows performing scattering correction with 3D avatar used for patient specific modeling.

FIG. 19 gives simulated images of the water elliptic tube presenting axes of 500 mm and of 370 mm, corresponding to simulation of an obese patient, surrounding the thin human phantom. On the left of FIG. 19, there is the total image, including both direct signal and scattering (self-scattering and cross-scattering signals), whereas on the right of FIG. 19, there is the denoised and corrected image with 3D avatar used for patient specific modeling where it can be seen that the different bones (ribs, spine, . . . ) are notably more easily detected on the corrected image than on the raw total image.

The obtained PSNR with this third embodiment is comparable to the one obtained with the predetermined database of scatter matrices of first and second embodiments, first embodiment being a little less performant than second embodiment but much faster. Therefore, the improvement of image quality is comparable. The use of a 3D avatar first will allow for getting rid of this whole database of numerous matrices, and second should even improve to a larger scale the image quality than the use of the predetermined database of scatter matrices, especially when the 3D avatar will become even more realistic than it is today. Some progresses are still waited for in the development of the 3D avatar in the future.

The invention has been described with reference to preferred embodiments. However, many variations are possible within the scope of the invention.

The invention claimed is:

1. A method of radiography of an organ of a patient, the method comprising:
    first vertical scanning said organ by a first radiation source and a first detector cooperating to make a first two-dimensional raw image of said organ;
    second vertical scanning said organ by a second radiation source and a second detector cooperating to make a second two-dimensional raw image of said organ, said first vertical scanning and said second vertical scanning being performed synchronously, said first and second raw images viewing said organ of said patient according to different angles of incidence; and performing computed correction processing on both said first and second raw images, on at least part of data associated with scanned patient height for at least overweight or obese patients, to reduce, between first and second corrected images, cross-scattering existing between said first and second raw images, said computed correction processing on both said first and second raw images comprising:

making a patient-specific model, using at least both of the first and second raw images as patient-specific data, the patient-specific model being a three-dimensional (3D) voxelized reconstruction, obtained from deformation of a generic model to patient-specific radiographic projections corresponding to the first and second raw images, determining a patient-specific representation of radiation scattering by making said patient specific model by directly simulating scatter signals scattered by the 3D voxelized reconstructions, and processing said determined patient-specific radiation scattering representation on both said first and second 2D raw images to obtain said first and second corrected images.

2. The method of radiography of the organ of the patient according to claim 1, wherein said computed correction processing is performed to also reduce, both in said first and second corrected images, respective self-scattering existing in both said first and second raw images.

3. The method of radiography of the organ of the patient according to claim 1, further comprising, before said computed correction processing:

a first screening, based on at least a first patient parameter representative of global patient corpulence, by one of: (i) electing said patient when said patient corresponds to an overweight or obese patient, and (ii) discarding said patient when said patient corresponds to a standard or underweight patient;

a second screening (i) for said elected patient, for each of the first and second raw images, by determining a location and an extent of the scanned patient height to which said computed correction processing is to be applied when a ratio of detected radiation that has been cross-scattered over total detected radiation exceeds a predetermined threshold, based on at least a second patient parameter representative of patient corpulence as a function of the scanned patient height, and (ii) for said discarded patient, keeping unchanged said first and second raw images without applying said computed correction processing on the first and second raw images;

performing, for said elected patient only and not for said discarded patient, for each of the first and second raw images, only on the data associated with said determined scanned patient height, said computed correction processing on each of the first and second raw images to obtain a first portion of said first and second corrected images, while keeping unchanged said first and second raw images elsewhere on the data associated with scanned patient height to obtain a second portion of said first and second corrected images equal to a corresponding part of said first and second raw images; and combining, for said elected patient only and not for said discarded patient, said first and second portions to get complete said first and second corrected images.

4. The method of radiography of the organ of the patient according to claim 3, wherein said first patient parameter is a patient base mass index, and/or wherein said second patient parameter is the patient thickness, either along a first direction going from the center of said first radiation source to the center of said first detector for the first raw image or along a second direction going from the center of said second radiation source to the center of said second detector for the second raw image, as a function of the scanned patient height.

5. The method of radiography of the organ of the patient according to claim 4, wherein under-sampling is performed with an under-sampling factor of at least 10, and/or wherein resulting under-sampled image pixel size is at least 1 mm.

6. The method of radiography of the organ of the patient according to claim 1, further comprising:

before said computed correction processing, dividing each of the first and second raw images into a set of raw sub-images along the scanned patient height to be corrected;

for each raw sub-image of said respective raw image, performing the computed correction processing on said raw sub-image including:

making an under-sampled patient specific model, as compared to a sample rate of said raw sub-image, determining an under-sampled patient-specific representation of radiation scattering by making said under-sampled patient specific model, over-sampling said determined under-sampled patient-specific radiation scattering representation to obtain a same sample rate as the raw sub-image, and processing said over-sampled patient-specific radiation scattering representation on said raw sub-image to obtain a corrected sub-image; and after processing said computed correction on all of the raw sub-images of said respective raw image, recombining all of the corrected sub-images to obtain the respective corrected image.

7. The method of radiography of the organ of the patient according to claim 6, wherein said determining the under-sampled patient-specific representation includes computing an under-sampled scattered sub-image corresponding to scattered only radiation by using a patient-specific scatter matrix representing radiation scattering by said under-sampled patient specific model, wherein said processing the over-sampled patient-specific radiation includes subtracting an over-sampled scattered sub-image from said raw sub-image to obtain said corrected sub-image, wherein said patient-specific scatter matrix is inverted before being multiplied by an image vector obtained by concatenating the two raw images, from the first pixel of one line of one of the two raw images to the last pixel the corresponding line of the other of the two raw images.

8. The method of radiography of the organ of the patient according to claim 6, wherein making said patient-specific model for each of the sub-images corresponds to a nearest ellipse or to a linear combination of nearest ellipses among a predetermined family of ellipses, and wherein said determining the under-sampled patient-specific representation of radiation scattering includes one of: (i) selecting, in a predetermined database of matrices respectively representing radiation scattering by the ellipses of said predetermined family, one matrix, and inverting the one matrix so that said inverse matrix represents cancellation of radiation scattering by said nearer ellipse, the inverse matrix thereby becoming a patient specific inverse matrix, and (ii) computing, in a predetermined database of matrices respectively representing radiation scattering by the ellipses of said predetermined family, the inverse of a linear combination of matrices respectively representing radiation scattering by said nearest ellipses of said linear combination of nearest ellipses, the inverse of linear combination of matrices thereby representing cancellation of radiation scattering by said nearest ellipses of said linear combination of nearest ellipses and becoming a patient-specific inverse matrix.

9. The method of radiography of the organ of the patient according to claim 8, wherein said predetermined family comprises ellipses of different sizes, different positions within a radiography apparatus where the radiography method is performed, and different orientations with respect to said radiography apparatus, and
wherein the density of said ellipses is equal to the density of water at a pressure of 1 bar and at a temperature of 20° C.

10. The method of radiography of the organ of the patient according to claim 9, wherein the number of sizes is comprised between 30 and 60, the greatest ellipse axis being above 30 cm, the smallest ellipse axis being above 15 cm, and/or the number of orientations is comprised between 3 and 5, and/or the number of positions is comprised between 5 and 200.

11. The method of radiography of the organ of the patient according to claim 1, further comprising:
before said computed correction processing, dividing each of the first and second raw images into a set of raw sub-images along scanned patient height to be corrected; and
for each raw sub-image of said respective raw image, performing the computed correction processing on said raw sub-image including:
making another patient-specific model, with a same sample rate as a sample rate of said raw sub-image,
determining another patient-specific representation of radiation scattering by making said other patient specific model, with the same sample rate as the sample rate of said raw sub-image, and
processing said patient-specific radiation scattering representation on said raw sub-image to obtain a corrected sub-image; and
after processing said computed correction on all of the raw sub-images of said raw image, recombining all of the corrected sub-images to obtain the corrected image.

12. The method of radiography of the organ of the patient according to claim 11, wherein said determining the patient-specific representation of radiation includes selecting or computing a patient-specific inverse matrix representing cancellation of radiation scattering by making said patient-specific model, and
wherein said processing the patient-specific radiation scattering representation includes multiplying said raw sub-image by said patient-specific inverse matrix to obtain said corrected sub-image.

13. The method of radiography of the organ of the patient according to claim 1, further comprising:
making an under-sampled patient specific model, as compared to a sample rate of said respective raw image;
determining an under-sampled patient-specific representation of radiation scattering by making said under-sampled patient specific model;
over-sampling said determined under-sampled patient-specific radiation scattering representation to obtain a same sample rate as said respective raw image; and
processing said over-sampled patient-specific radiation scattering representation on said respective raw image s to obtain the respective corrected image.

14. The method of radiography of the organ of the patient according to claim 13, wherein said determining the under-sampled patient-specific representation includes
making a unique and predetermined patient-specific 3D avatar at least from both of the first and second raw images, and
vertically scanning the patient-specific 3D avatar in the same conditions as the patient but for a lower resolution allowing for under-sampling, thereby computing an under-sampled scattered image corresponding to scattered only radiation by the patient-specific 3D avatar, and
wherein said processing the over-sampled patient-specific radiation scattering representation includes subtracting an over-sampled scattered image from said raw image to obtain said respective corrected image.

15. The method of radiography of the organ of the patient according to claim 14, wherein said determining the under-sampled patient-specific representation includes one or more of:
(i) making a unique and predetermined patient-specific 3D avatar using only both of the first and second raw images as the patient-specific data, and
(ii) making a unique and predetermined patient-specific 3D avatar using additional patient specific data, apart from the first and second raw images used as the patient-specific data, coming from one or more of: (i) magnetic resonance imaging and (ii) computerized tomography scan.

16. The method of radiography of the organ of the patient according to claim 13, wherein under-sampling is performed with an under-sampling factor of at least 10, and/or
wherein resulting under-sampled image pixel size is at least 1 mm.

17. The method of radiography of the organ of the patient according to claim 1, wherein an X-ray spectrum of the first and second radiation sources, used to determine said patient-specific representation of radiation scattering, has an energy comprised between 50 keV and 70 keV, and the first and second radiation sources are monochromatic sources.

18. The method of radiography of the organ of the patient according to claim 1, wherein said method of radiography is performed with an overweight patient or with an obese patient.

19. The method of radiography of the organ of the patient according to claim 1, wherein a collimation tunnel is disposed upstream of each of the first and second detectors to further reduce cross-scattering on said first and second corrected images.

20. The method of radiography of the organ of the patient according to claim 1, further comprising, before said making the patient-specific model from both of the first and second raw images, denoising said first and second raw images, to further reduce excessive noise created by one or more of: (i)

cross-scattering and (ii) self-scattering on said first and second corrected images, said denoising being bilateral filtering of said first and second raw images.

21. The method of radiography of the organ of the patient according to claim 1, wherein said first and second detectors are multi-energy counting detectors.

22. The method of radiography of the organ of the patient according to claim 1, wherein said first and second detectors are mono-energy counting detectors.

23. The method of radiography of the organ of the patient according to claim 1, wherein said first and second detectors have more than 3000 pixels per line, and/or
   wherein said first and second detectors have between 1 and 100 lines, and/or
   wherein said first and second detectors have a pixel dimension comprised between 50 μm and 200 μm.

24. The method of radiography of the organ of the patient according to claim 1, wherein said determining the patient-specific representation uses a predetermined database of matrices respectively representing radiation scattering by making a patient generic model, the matrices being based on Monte-Carlo simulations of X-ray scattering.

25. The method of radiography of the organ of the patient according to claim 24, wherein said Monte-Carlo simulations of X-ray scattering are performed with an X-ray spectrum of the first and second radiation sources having an energy comprised between 50 keV and 70 keV, the first and second radiation sources being monochromatic sources.

26. The method of radiography of the organ of the patient according to claim 1, wherein said first and second raw images view said organ of said patient according to two directions orthogonal to each other.

27. The method of radiography of the organ of the patient according to claim 1, wherein a vertical gap is defined between said first radiation source and the first detector and said second radiation source and the second detector, such that said first vertical scanning and said second vertical scanning are performed synchronously, to further reduce cross-scattering between said first and second raw images.

28. A radiography apparatus comprising:
   a first radiation source and a first detector cooperating to perform first vertical scanning of an organ of a patient to make a first two-dimensional raw image of said organ;
   a second radiation source and a second detector cooperating to perform second vertical scanning of the organ to make a second two-dimensional raw image of the organ, said first vertical scanning and said second vertical scanning being performed synchronously, said first and second raw images viewing said organ of said patient according to different angles of incidence; and
   one or more processors configured to perform computed correction processing on both said first and second raw images, on at least part of data associated with scanned patient height for at least overweight or obese patients, to reduce, between first and second corrected images, cross-scattering existing between said first and second raw images, said computed correction processing on both said first and second raw images comprising:
      making a patient-specific model, using at least both of the first and second raw images as patient-specific data, the patient-specific model being a three-dimensional (3D) voxelized reconstruction, obtained from deformation of a generic model to patient-specific radiographic projections corresponding to the first and second raw images,
      determining a patient-specific representation of radiation scattering by making said patient specific model by directly simulating scatter signals scattered by the 3D voxelized reconstructions, and
      processing said determined patient-specific radiation scattering representation on both said first and second 2D raw images to obtain said first and second corrected images.

29. A method of radiography of an organ of a patient, the method comprising:
   first vertical scanning of said organ by a first radiation source and a first detector cooperating to make a first two-dimensional raw image of said organ;
   second vertical scanning of said organ by a second radiation source and a second detector cooperating to make a second two-dimensional raw image of said organ, said first vertical scanning and said second vertical scanning being performed synchronously, said first and second raw images viewing said organ of said patient according to different angles of incidence; and
   performing computed correction processing on both said first and second raw images, on at least part of data associated with scanned patient height, for at least overweight or obese patients, to reduce, between first and second corrected images, cross-scattering existing between said first and second raw images, said computed correction processing on both said first and second raw images comprising:
      making a patient-specific model, using at least both of the first and second raw images, said patient-specific model being a voxelized geometry corresponding to a combination of simple geometries,
      obtaining a patient-specific scatter matrix representing radiation scattering of said patient-specific model from a pre-computed base of matrices corresponding to said simple geometries by interpolation between matrices among the pre-computed base of matrices, the pre-computed base of matrices being obtained with simulations,
      determining a patient-specific representation of radiation scattering by said patient-specific model, by simulating the radiation scattering of said voxelized geometry based on the patient-specific scatter matrix, and
      processing said patient-specific radiation scattering representation on both said first and second raw images to obtain said first and second corrected images.

30. The method of radiography of the organ of the patient according to claim 29, wherein the patient-specific data uses only the first and second raw images.

* * * * *